(12) United States Patent
Lee et al.

(10) Patent No.: US 9,632,053 B2
(45) Date of Patent: Apr. 25, 2017

(54) ANALYTE SENSING DEVICE

(71) Applicant: Senova Systems, Inc., Sunnyvale, CA (US)

(72) Inventors: Eric Lee, Sunnyvale, CA (US); Lee Leonard, Sunnyvale, CA (US); Thang Huy Vu, San Jose, CA (US); James Alan Andrew, Los Altos, CA (US)

(73) Assignee: Parker-Hannifin Corporation, Cleveland, OH (US)

( * ) Notice: Subject to any disclaimer, the term of this patent is extended or adjusted under 35 U.S.C. 154(b) by 0 days.

(21) Appl. No.: 14/383,873

(22) PCT Filed: Mar. 8, 2013

(86) PCT No.: PCT/US2013/029746
§ 371 (c)(1),
(2) Date: Sep. 8, 2014

(87) PCT Pub. No.: WO2013/134582
PCT Pub. Date: Sep. 12, 2013

(65) Prior Publication Data
US 2015/0014164 A1    Jan. 15, 2015

Related U.S. Application Data

(60) Provisional application No. 61/608,483, filed on Mar. 8, 2012.

(51) Int. Cl.
*G01N 27/30* (2006.01)
*G01N 27/416* (2006.01)

(52) U.S. Cl.
CPC .......... *G01N 27/30* (2013.01); *G01N 27/302* (2013.01); *G01N 27/4167* (2013.01)

(58) Field of Classification Search
CPC .......... G01N 27/4166; G01N 27/4167; G01N 27/302; G01N 27/30
See application file for complete search history.

(56) References Cited

U.S. PATENT DOCUMENTS

| 7,182,847 B1* | 2/2007 | Millar | G01N 27/333 204/433 |
|---|---|---|---|
| 2011/0048971 A1* | 3/2011 | Bower | G01N 27/4035 205/787.5 |
| 2012/0090995 A1* | 4/2012 | Leonard | G01N 27/4166 204/406 |
| 2012/0144894 A1* | 6/2012 | Trapp | G01N 35/00693 73/1.06 |
| 2015/0114836 A1* | 4/2015 | Clark | G01N 27/302 204/403.02 |

* cited by examiner

*Primary Examiner* — Gurpreet Kaur
(74) *Attorney, Agent, or Firm* — David R. Conklin; Kirkton McConkie

(57) ABSTRACT

Analyte sensing devices suitable for measuring pH or other analytes are provided in a variety of form factors, including a hand-held device.

17 Claims, 19 Drawing Sheets

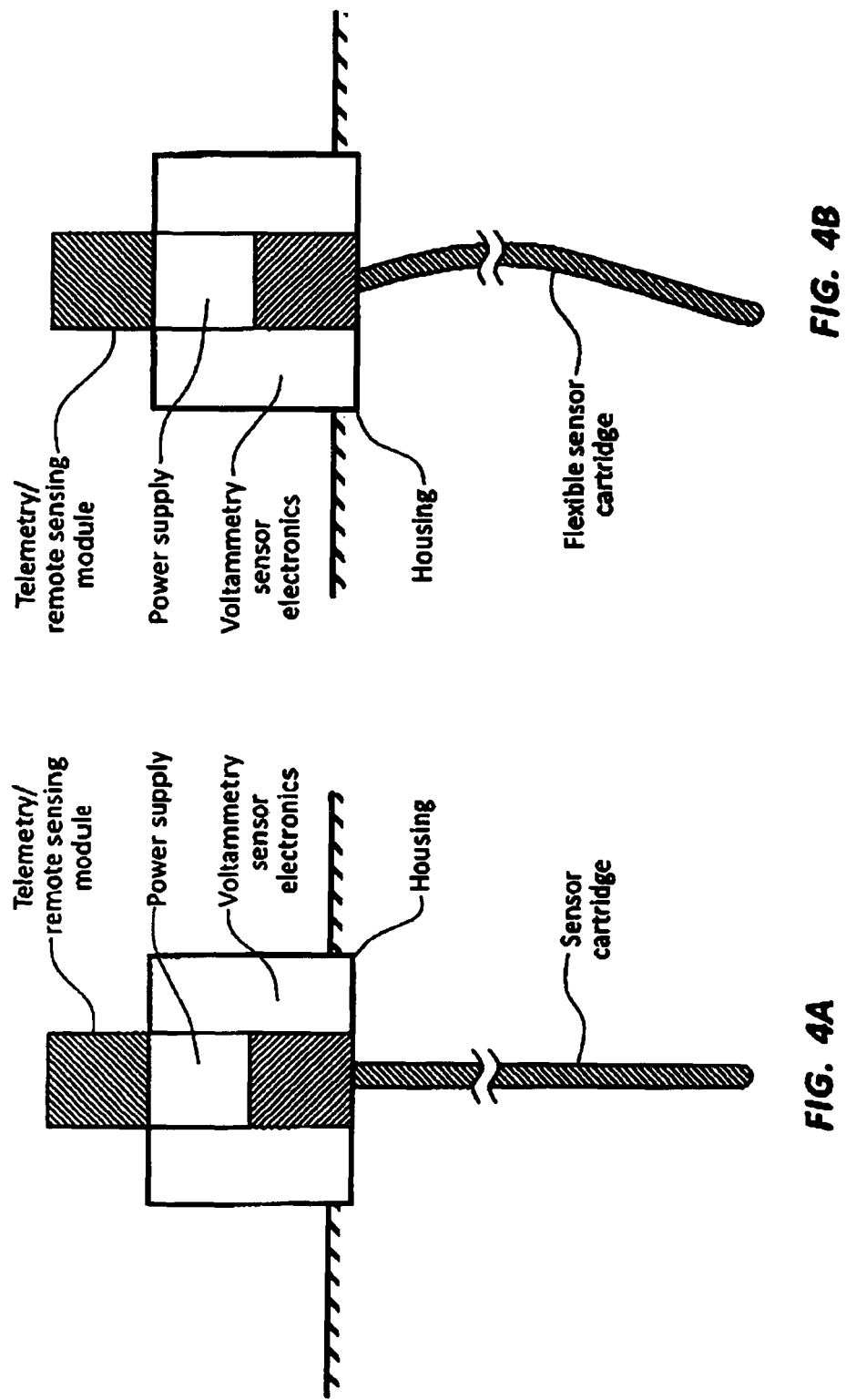

ANALYTE SENSING DEVICE

This application is a National Stage of International Application No. PCT/US2013/029746, filed Mar. 8, 2013, and entitled ANALYTE SENSING DEVICE, which claims the benefit of United States Provisional Application Nos. 61/608,483, filed Mar. 8, 2012. This application claims priority to and incorporates herein by reference the above-referenced application in its entirety.

BACKGROUND OF THE INVENTION

The present invention relates generally to technology for detecting an analyte. In various embodiments, the invention relates to devices for measuring pH, the potential of hydrogen, which is a measure of the acidity or alkalinity of a solution. The pH of a solution is determined by the concentration of dissolved hydrogen ions ($H^+$) (also referred to as hydronium ions, $H_3O^+$) within the solution. As the concentration of dissolved hydrogen ions within the solution increases, the solution becomes more acidic. Conversely, the solution becomes more basic as the concentration of dissolved hydrogen ions within the solution decreases. The concentration of dissolved hydrogen ions within a solution has traditionally been measured with a glass electrode connected to an electronic meter that displays the pH reading. Traditionally the terms "probe" and "electrode" have been used interchangeably to describe a functional grouping of component electrodes. As used herein, the term "electrode" is used to refer to a specific electrode in a probe, i.e., such as a "working electrode", a "reference electrode", or a "counter electrode", and "probe" refers to a functional grouping of electrodes sufficient to generate a signal that can be processed to generate a reading indicative of the concentration of an analyte of interest in a solution.

The traditional glass pH probe has a working electrode (WE) that is an ion-selective electrode made of a fragile, doped glass membrane sensitive to hydrogen ions. The pH-responsive glass membrane is the primary analyte sensing element in this type of probe and so is referred to as the "working" electrode. Hydrogen ions within the sample solution bind to the outside of the glass membrane, thereby causing a change in potential on the interior surface of the membrane. This change in potential is measured against the constant potential of a conventional reference electrode (RE), such as an electrode based on silver/silver chloride. The difference in potential is then correlated to a pH value by plotting the difference on a calibration curve. The calibration curve is created through a tedious, multistep process whereby the user plots changes in potential for various known buffer standards. Traditional pH meters are based on this principle.

The response of traditional glass working electrodes (and probes and meters containing them) to pH is unstable, and glass probes periodically require careful calibration involving tedious, time-consuming processes, multiple reagents, and a trained operator. The special properties and construction of the glass probes further require that the glass membrane be kept wet at all times. Thus, routine care of the glass probe requires cumbersome and costly storage, maintenance, and regular calibration performed by a trained operator to ensure proper working performance.

In addition to tedious maintenance and storage requirements, traditional glass probes are fragile, thereby limiting the fields of application of the glass probe. In particular, the fragile nature of the glass probe makes it unsuitable for use in food and beverage applications, as well as use in unattended, harsh, or hazardous environments. Accordingly, there is a need in the art for pH probes and meters (as well as other analyte probes and meters) that address and overcome the limitations of traditional pH probes and meters employing the glass probe. Voltammetry-based analyte sensing systems have been proposed as a replacement for the glass probe; however, those systems were costly and difficult to use when first developed (see Wrighton, U.S. Pat. No. 5,223,117).

Significant advances were made in both theory and research laboratory practice of voltammetry-based analyte sensing systems when researchers discovered that carbon could replace gold as the conductive substrate and, moreover, that, regardless of the substrate, mixtures of redox active materials could be used in voltammetric systems (see PCT Pub. Nos. 2005/066618 and 2005/085825). One particularly intriguing proposal by these researchers was that a mixture of "analyte-sensitive" redox active materials (ASMs) and "analyte-insensitive" redox active materials (AIMs) could be attached to a conductive substrate and effectively convert it into both a WE (signal generated by the ASM) and a reference electrode (RE) (signal generated by the AIM). No significant advances, however, in either theory or practice were made for some time after these initial proposals and research (see, e.g., PCT Pub. Nos. 2007/034131 and 2008/154409).

Another significant advance in the field occurred when scientists discovered that, in practice, no redox active material is completely "analyte-insensitive" and that practical application of voltammetric technology should focus on WEs without AIMs. These scientists also discovered, however, that, regardless of whether a redox active material was characterized as an ASM or AIM (collectively referred to herein as "redox active materials" or "RAMs"), it could be made truly analyte-insensitive by sequestration in an ionic medium or "constant chemical environment". This discovery led to the analyte-insensitive electrode or AIE, which could not only be used as a replacement of the conventional RE in traditional pH measuring systems but could also be used with WEs based on voltammetry. See PCT Pub. No. 2010/104962. Soon after these discoveries, pH meters suitable for use on the laboratory bench-top and for important research and development applications were created. See PCT Pub. Nos. 2010/111531 and 2010/118156. More recent advances in ASM chemistry, electrode design, and fabrication technology have produced WEs and other components that collectively provide improved accuracy, minimal signal drift, and convenience of use such as wet-dry reversibility. See co-pending PCT application US2013/023029, incorporated herein by reference.

There remains a need in the art for electrodes, probes, pH meters, and other analyte sensing devices based on voltammetry that provide precise measurements over extended lifetimes and that can be used under a wider variety of conditions by relatively unskilled workers. In addition, conventional pH electrodes are limited to sizes and shapes required by glass fabrication technology. Thus the great majority of pH electrodes in use are straight, rigid rods of limited length. An alternative pH sensor that can be packaged in flexible, semi-rigid, or user-configurable form factors that also incorporate benefits from the abovementioned recent advances would enable many new applications. The present invention meets these needs.

SUMMARY OF THE INVENTION

The present invention relates generally to voltammetric sensors comprising novel redox-active working electrodes, reference electrodes, and counter electrodes. The present invention also provides pH meters and other analyte sensing devices comprising voltammetric sensors. In some embodiments, a hand-held pH meter comprises a sensor cartridge that houses a working electrode, a reference electrode, a counter electrode, and optionally a temperature sensor arranged in a cluster. The cartridge is connected reversibly to an enclosure, referred to herein as the head unit, that houses circuit boards, connectors, control buttons, and a display. Electronics in the head unit are designed to perform square wave voltammetry, capture the response from the electrode cluster, and convert that response to the pH (or other analyte concentration) for display or for further transmission. The use of a connector allows head units and cartridges to be operated interchangeably, and facilitates cartridge replacement.

In other aspects, the invention provides sensor cartridges of various form factors beyond those possible with conventional glass electrodes. In some embodiments, the sensor cartridge comprises a flexible body, wherein the sensor cluster is located at a distal end of the body. This allows measurement at locations normally inaccessible to glass electrodes because of their rigidity, straight form factor, and inherent fragility, in addition to the difficulty of performing routine calibration and maintenance. In other embodiments, the sensor cartridge is designed to have a diameter smaller than 12 mm, e.g., 5 mm or less, to enable measurement of small analyte volumes, as may be contained in, for example, Eppendorf tubes or wells in a multi-well plate.

In other aspects, the invention provides a user interface (UI) comprising means for controlling the operation of the voltammetry measurement and displaying measurement results, including pH, temperature, and optionally other information, such as the current peak position and signal strength generated by the working electrode for the analyte under test.

In yet other aspects, the invention provides a modified reference electrode. In some embodiments, the reference electrode comprises an Ag/AgCl half cell and a reference junction comprising a composite material formed using a room temperature ionic liquid (RTIL), a polymer, and optionally a carbon allotrope.

These and other aspects and embodiments of the invention are illustrated in the accompanying drawings and described in detail below.

BRIEF DESCRIPTION OF THE FIGURES

FIG. 3 shows two configurations for positioning voltammetric sensor electronics in relation to the sensor module in an illustrative embodiment of a 12-mm diameter removable sensor cartridge having a custom plug that inserts into the custom connector of a head unit as shown in FIG. 1 in accordance with representative embodiments of the invention.

FIG. 4 shows schematically two pH transmitters with telemetry or remote sensing capabilities and incorporating voltammetric sensors in a rigid or flexible cartridge in accordance with representative embodiments of the invention. FIG. 4A shows a transmitter with a rigid sensor cartridge, and FIG. 4B shows a transmitter with a flexible sensor cartridge. Both are shown to have the sensor cartridge immersed in liquid or embedded in solid, and with the transmitter exposed to facilitate telemetric communication. The sensor cartridge is connected to voltammetry sensor electronics whose output is transmitted by the telemetry/remote sensing module. A power supply is provided for operation of the system.

which corresponds to the entire pH range. In this example, one can observe the peak position is approximately −0.4V. The Track Scan (B) shows a more narrow scan window centered at approximately −0.4 V plus and minus 300 mV i.e. −765 to −165 mV. In this example (B), one can observe that the peak position is more precisely located at approximately −465 mV.

Figure 12A:
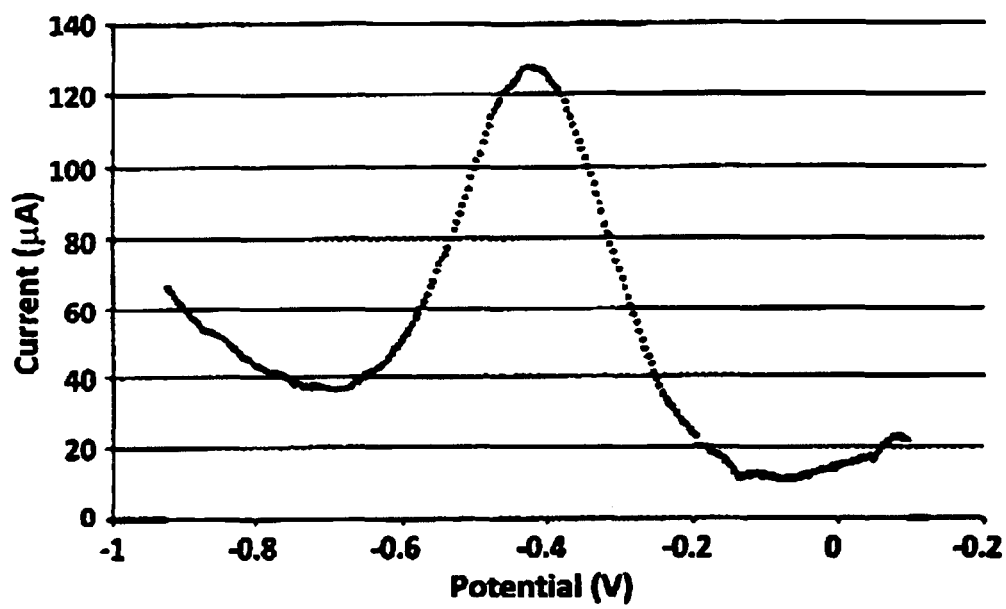
FIG. 12 illustrates a method of the invention for detecting a signal peak rapidly by means of seek scan (A) with a scan window of approximately 1200 mV (i.e. −1V to +0.2 V)
Figure 12B:
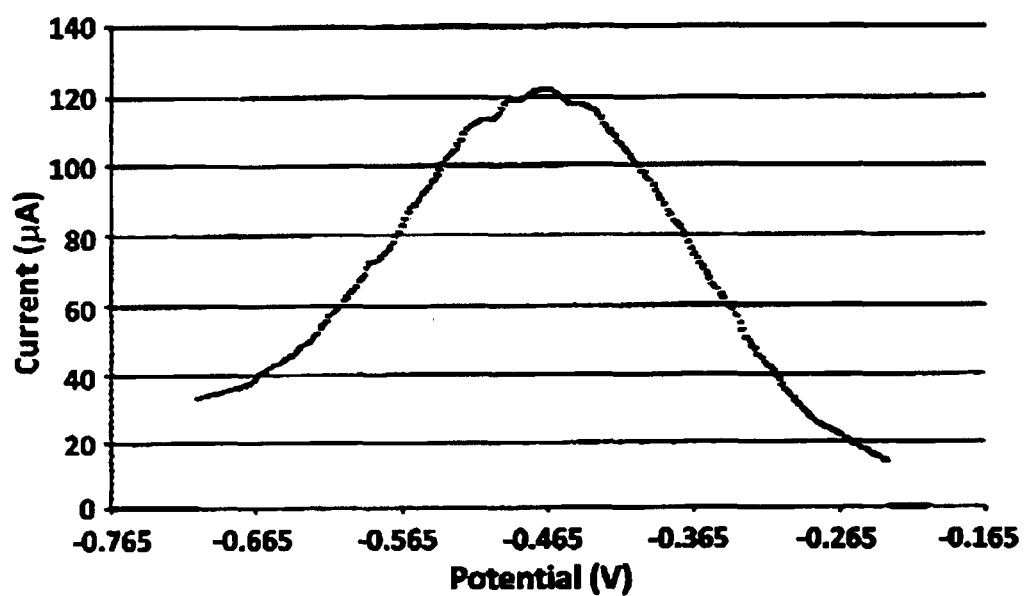
Figure 13:
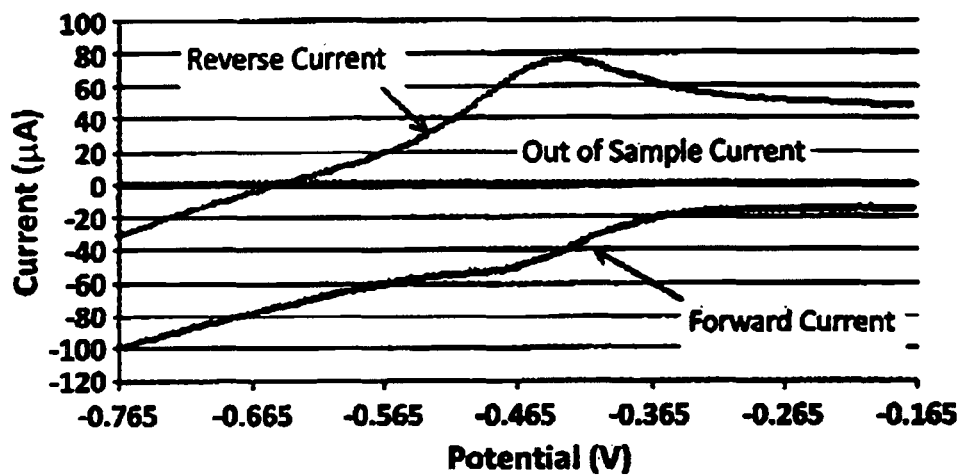

FIG. 13 depicts representative signals of tracking scan generated by the voltammetric sensor in pH 7 buffer. The subtraction between the forward and reverse current can be taken to generate the difference current (see FIG. 12). "Out of Sample" current indicates a scanner is not in contact with an analyte sample in accordance with a representative embodiment of the invention.

Figure 14:
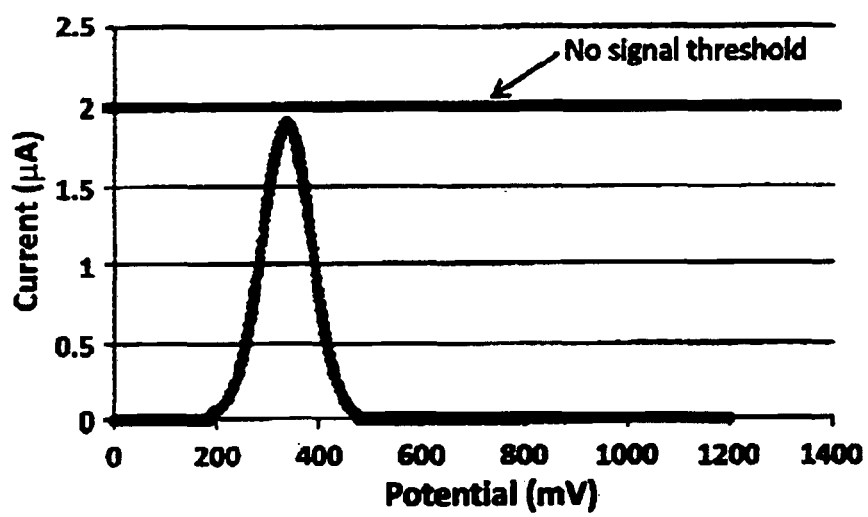

FIG. 14 shows signal processing in which a peak is detected but is below a signal threshold of 2 microamps (μA), such that the pH scanner reports a "no signal" message on the LCD in accordance with a representative embodiment of the present invention.

Figure 15:
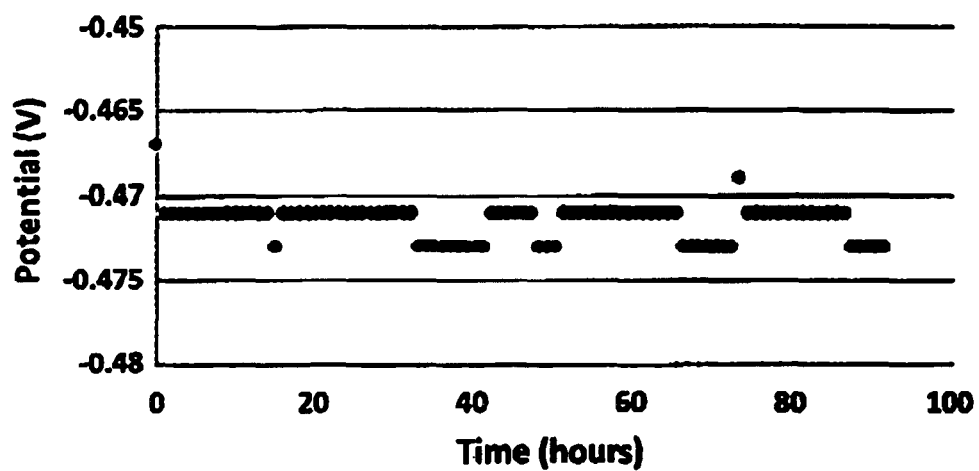
Figure 16:
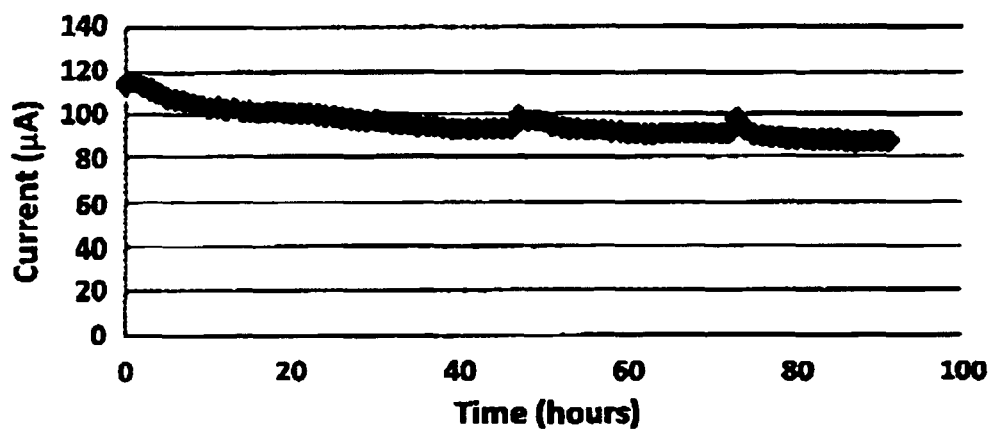

FIG. 15 shows representative stability characteristics of a voltammetric sensor when tested in BDH buffer pH 7 for 90 hours. The peak potential is stable at −0.471±0.002V FIG. 16 shows representative signal strength characteristics from the same voltammetric sensor in FIG. 15 when tested in BDH buffer pH 7. The current after 80 hours of scanning is at 87 μA.

Figure 2:
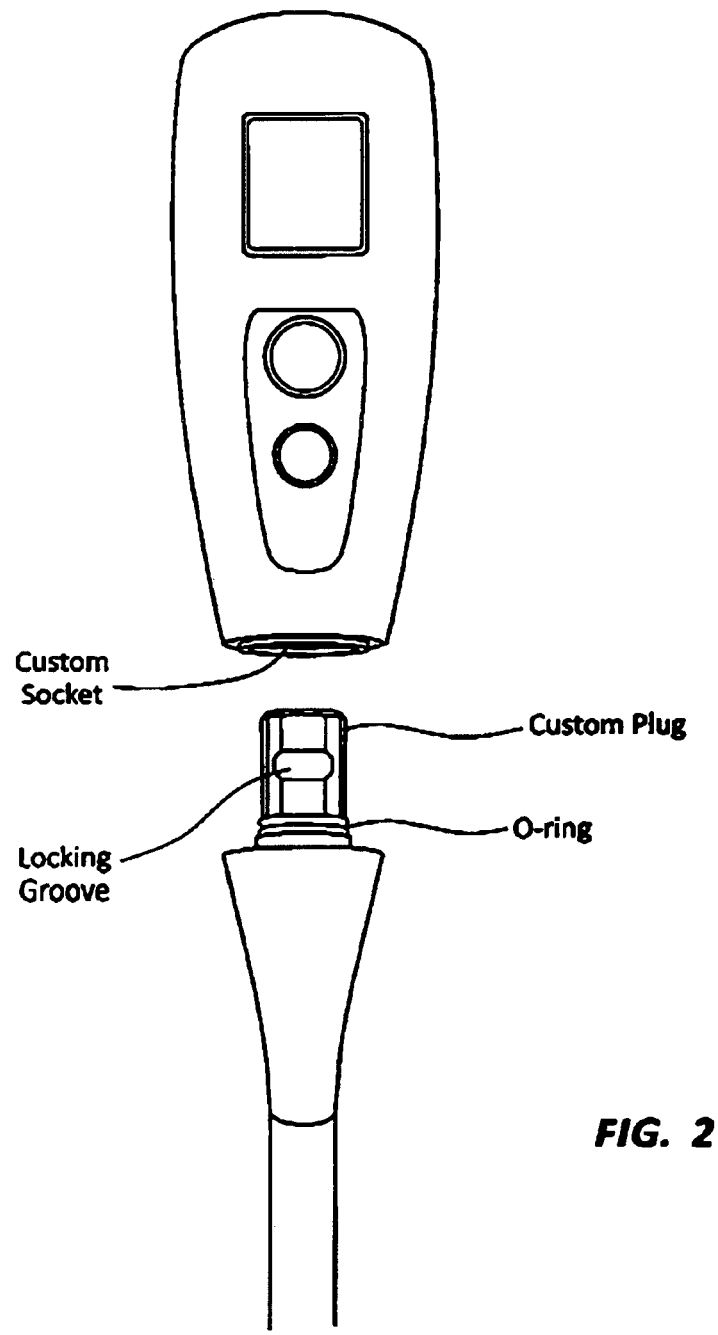
FIG. 2 shows a custom connector that consists of a mating plug and socket. The plug is on the cartridge end having male connector pins, a locking groove and an o-ring that creates a water-tight seal. The socket is located on the head having female pin connectors and cartridge release button located behind the head in accordance with a representative embodiment of the invention.
Figure 17:
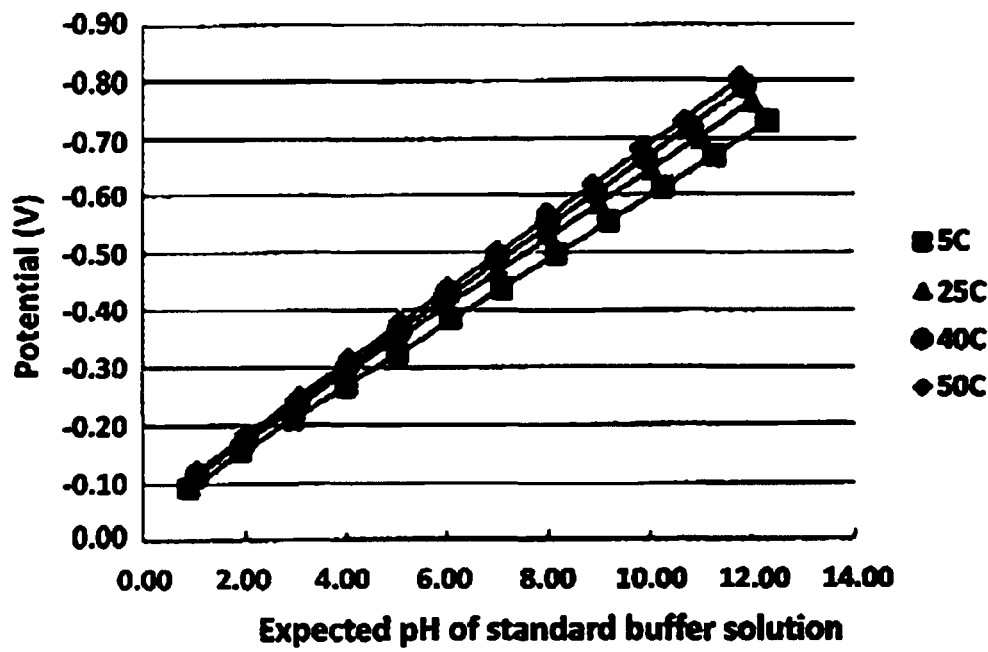

FIG. 17 shows representative relationships between peak potential and pH at various temperatures generated using BDH buffers and a sensor cartridge in the embodiment shown in FIG. 2A.

Figure 18:
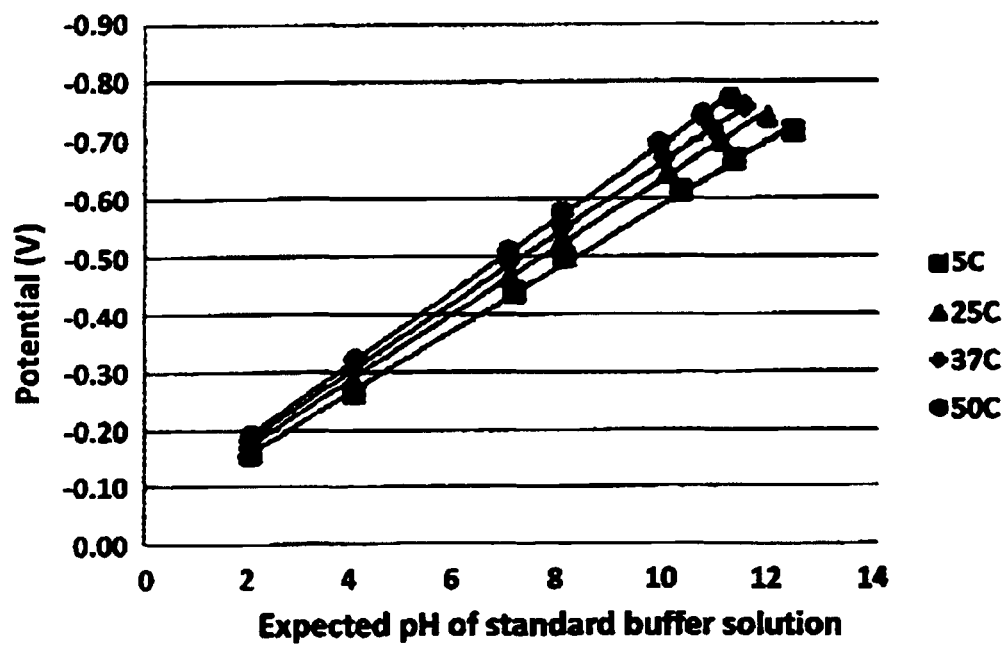

FIG. 18 shows representative relationships between peak potential and pH at various temperatures generated using BDH buffers and a sensor cartridge in the embodiment shown in FIG. 2B.

Figure 19:
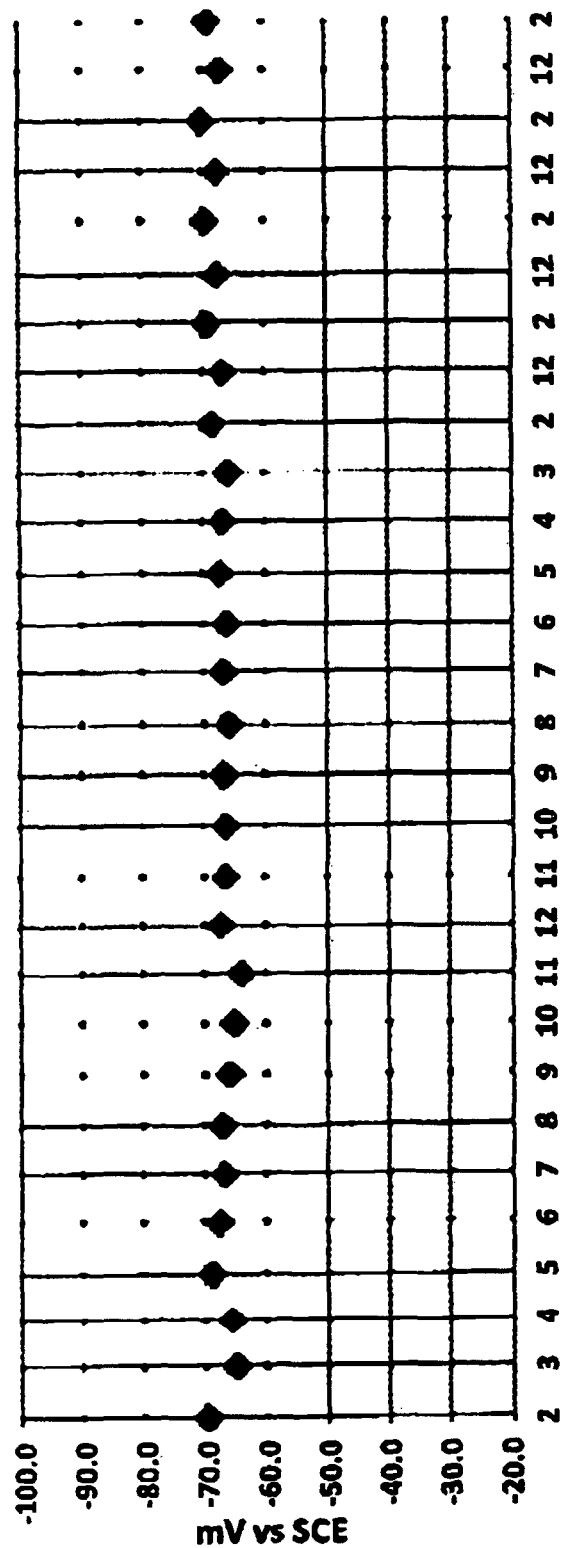

FIG. 19 shows the stability characteristic of a modified reference electrode against a Cole-Parmer calomel electrode (Cole-Parmer, EW-05990-50). The modified reference electrode potential is measured in BDH buffers from pH 2 to 12 in ascending and descending order as well as going between pH 2 and 12 several times.

Figure 20A:
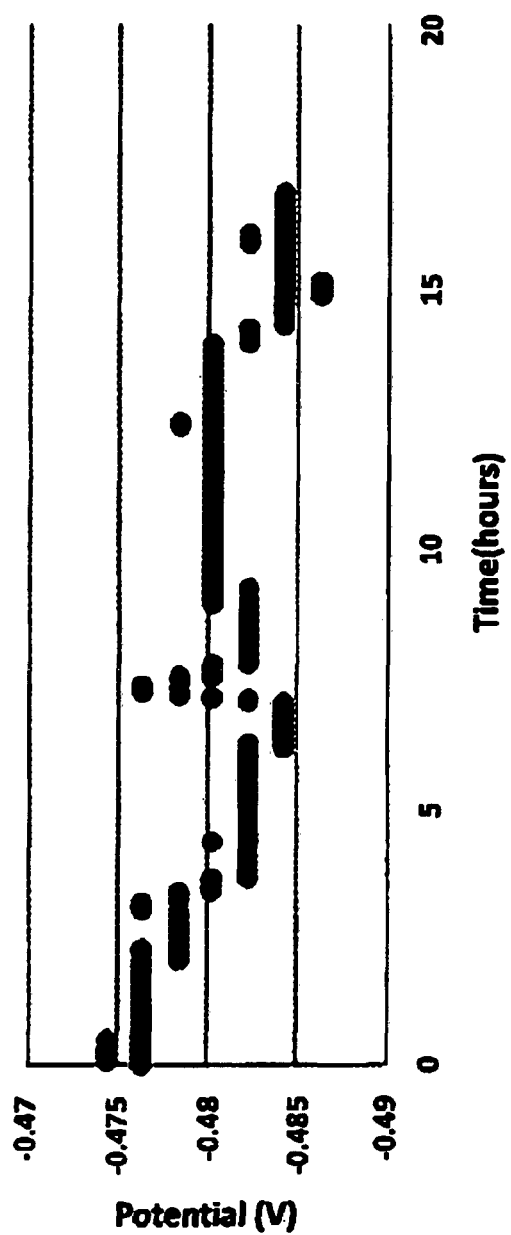

FIG. 20A shows the peak potential (PP) signal from an IWE of an analyte-insensitive electrode (see FIG. 6) in BDH buffer pH 7. A drift of 0.010V is observed between 0 and 17 hours.

Figure 20B:
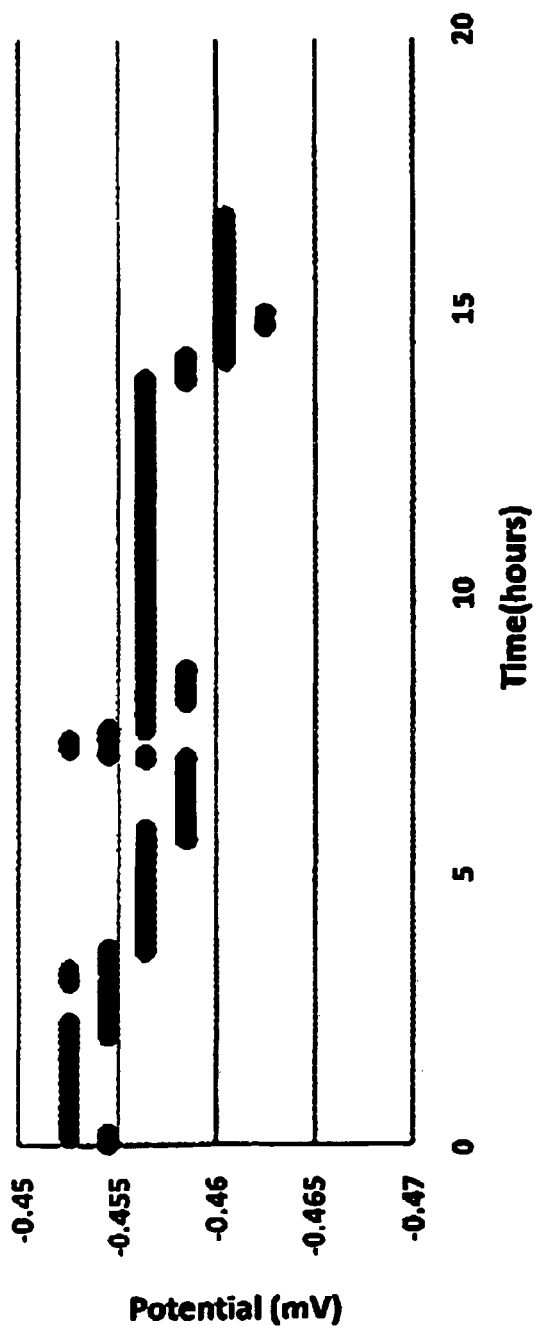

FIG. 20B shows the peak potential signal from an EWE of an analyte-insensitive electrode in BDH buffer pH 7. A drift of 0.010-0.012V is observed between 0 and 17 hours.

Figure 20C:
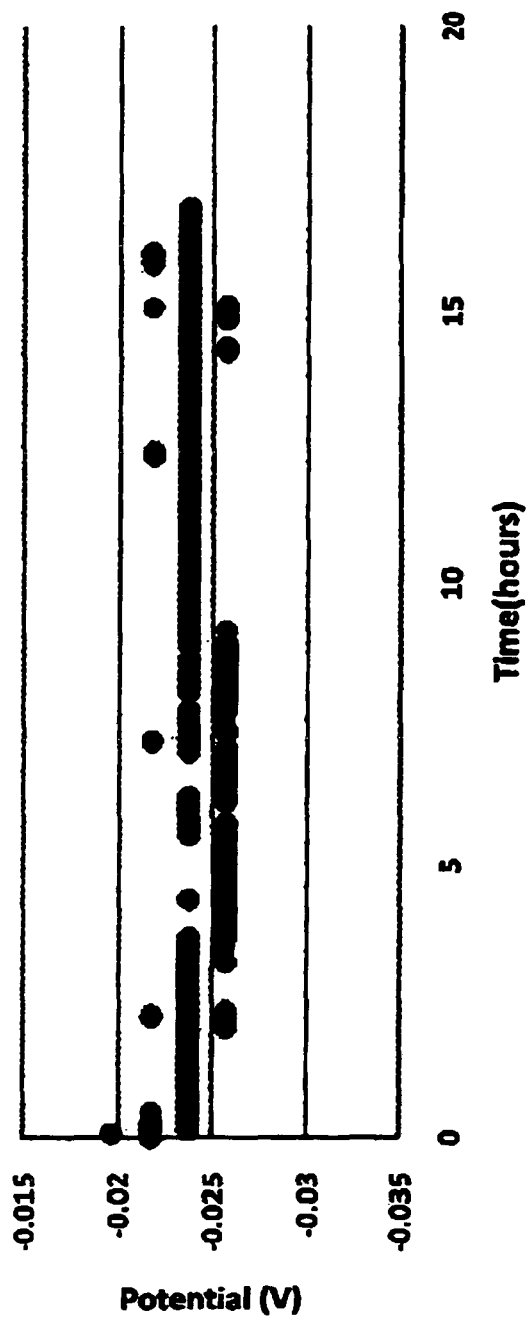

FIG. 20C shows the subtracted signal from the internal and external working electrodes of an analyte-insensitive electrode. This yields a stable potential at −0.025±0.002V over a period of 17 hours.

DETAILED DESCRIPTION OF THE INVENTION

The present invention provides instruments and components thereof for measuring analyte concentrations, especially pH, by means of voltammetric sensors in various form factors, using various signal processing methods and user interfaces.

DEFINITIONS

As used in the specification and the appended claims, the singular forms "a," "an" and "the" include plural referents unless the context dictates otherwise.

An "analyte" is a chemical species of interest present in a sample, the presence of which is detectable or the concentration of which is measurable using an analyte sensor system that incorporates a working electrode.

An "analyte-sensitive material" or "ASM" is a redox-active material that is sensitive or substantially sensitive to the presence or concentration of an analyte in a sample within those user-defined application-specific tolerances. "Substantially sensitive" to an analyte is used to mean sensitive within the tolerances required for a given application, as those tolerances are defined by an end user.

An "analyte-insensitive material" or "AIM" is a redox-active material that is insensitive or substantially insensitive to the presence or the concentration of an analyte in a sample. "Substantially insensitive" to an analyte is used to mean insensitive within the tolerances required for a given application, as those tolerances are defined by an end user.

An "analyte sensing device" is a sensor, a means to measure the signal from the sensor, and optionally a means to display that signal. A pH meter is a type of analyte sensing device. Thus, in some embodiments, an analyte sensing device includes a controller/processor unit, associated programs and algorithms, and a probe.

A "pseudo-reference electrode" or "PRE" is a type of electrode in the category of electrodes whose potentials vary predictably in accordance with the conditions of their environments. Once established, such correlation may be used to calculate an electrode potential for known conditions even if those conditions go beyond the relatively narrow range in which conventional reference electrodes are applicable, for example non-aqueous solutions or temperatures far from ambient. In those situations they provide a reasonably constant potential over the timescale of an electrochemical experiment, and the absolute potential of the PRE can be back-calibrated to a RE if required. Pseudo-reference electrodes typically do not comprise both halves of a redox couple. One example of a PRE is a silver wire (used commonly in non-aqueous electrochemistry). More recently, PREs have been used as a component of an AIE.

A "redox-active material" is a compound or composition that may be oxidized and reduced. "Redox activity" refers to either or both of those processes.

A "reference electrode" (RE) is an electrode used to establish the potential difference applied to the WE. Conventional REs have a certain fixed chemical composition and therefore a fixed electrochemical potential, thus allowing measurement of the potential difference applied to the WE in a known, controlled manner. An RE typically comprises two halves of a redox couple in contact with an electrolyte of fixed chemical composition and ionic strength. Because both halves of the redox couple are present and the composition of all the species involved is fixed, the system is maintained at equilibrium, and the potential drop (i.e., the measured voltage) across the electrode-electrolyte interface of the RE is then thermodynamically fixed and constant. For example a commonly used RE system is the Ag/AgCl/KCl system with a defined and constant concentration of KCl. The two half-cell reactions are therefore: $Ag^+ + e^- \rightarrow Ag$; and $AgCl + e^- \rightarrow Ag + Cl^-$. The overall cell reaction is therefore: $AgCl \rightarrow Ag^+ + Cl^-$ for which the Nernst equilibrium potential is given as: $E = E_0 - (RT/F)*\ln[Cl^-]$, where E is the measured RE potential, $E_0$ is the standard potential of the Ag/AgCl couple vs. the standard hydrogen electrode with all species at unit activity (by convention the standard hydrogen electrode is defined as having a potential of 0.0V); and R, T, and F are the universal gas constant, temperature, and Faraday constant, respectively, in appropriate units. Hence, the potential of this system depends only on the concentration (more strictly speaking the activity) of Cl⁻ ion present, which, if this is fixed, provides a stable, fixed potential. Many other RE systems are known in the art. It is imperative that the composition of the RE remains constant, and hence almost no current should be passed through the RE (otherwise electrolysis will occur and the composition of the RE will change), which necessitates the use of a third electrode, the counter electrode (CE), to complete the circuit. However, two-electrode configurations can be used in the special case where the WE is a microelectrode, having at least one dimension typically smaller than 100 micrometers. In this case, the currents passed at the WE are small, and therefore a two-electrode cell can be used with a RE, but without the need for a CE.

A "sensor" is an electrode or collection of electrodes that generates a signal in response to the presence of an analyte.

An "electrode" is a component of a probe.

A "probe" refers to a sensor that contains multiple electrodes. A probe can include, for example, a working electrode, a counter-electrode and a reference electrode (either a conventional reference electrode or a pseudo reference electrode). A probe can include, for example, a working electrode, a counter electrode and an analyte-insensitive electrode (an IWE and PRE).

A "working electrode" or "WE" is the electrode at which the electrochemical process for detecting the analyte of interest occurs. In a sensor, the working electrode may be sensitive to one or more analyte(s) in the test sample, or it may be chemically modified with analyte sensitive species/materials. The electrochemical response of the working electrode is measured after some perturbation to the system under study has been applied. For example, the perturbation may be the application of a potential difference to the WE that induces electron transfer to occur, and the resulting current at the WE is then recorded as a function of the applied potential (voltammetric mode). This example of mode of operation is illustrative and not exhaustive, as many other modes are known in the art. The WEs of the invention contain an ASM that can undergo a reversible electrochemical redox reaction dependent upon the concentration of analyte (hydrogen ions for a pH meter; other analytes for other analyte sensing devices) in a sample solution and an applied electrical potential. For example, where there is a high concentration of hydrogen ions present in a sample solution, the redox reaction occurs at a lower potential. Conversely, where there is a low concentration of hydrogen ions present in a sample solution, the redox reaction occurs at a higher potential. The relationship between these characteristic potentials and the sample solution pH is a function of the chemical identity of the ASM. An algorithm converts electrical potential to pH value to provide a means of determining the pH of an unknown sample.

An "analyte insensitive electrode" (AIE) is a special case of a reference electrode that derives a constant electrode potential by juxtaposing a redox-active WE with a constant chemical environment comprising a material with buffering properties. The constant chemical environment is, in turn, in ionic communication with but convectively separated from the analyte. The AIE provides a predictable signal useful as an internal standard (in other words, a standard internal to the system) with which an analyte-sensitive signal may be continuously compared, and therefore permit greater accuracy and reproducibility in determining analyte concentration. See PCT Application No. US2013/023029 and PCT Publication No. 2010/104962, incorporated herein by reference.

A "temperature sensor" allows for real time temperature measurement of the surrounding environment. An example of this is a resistance temperature detector (RTD), thermistor, or thermocouple.

With the above definitions in mind, the reader can better appreciate the various aspects and embodiments of the invention described below.

Generally, the voltammetric sensor technology of the invention utilizes a WE comprising a substrate to which is attached an analyte sensitive material (ASM). The ASM may itself be in a matrix. In some embodiments of the invention, the sensor technology also utilizes an AIE. In some instances, an AIE is provided that also comprises a substrate and a redox active material (RAM, which may be an ASM or AIM). In some aspects, the substrate for the ASM matrix material of the WE (or the RAM matrix material for the AIE) is or comprises carbon.

A variety of carbon substrates are suitable for use as substrate material in the electrodes of the present invention, including but not limited to carbon allotropes such as graphites, including pyrolytic graphite and isotropic graphite, amorphous carbon, carbon black, single- or multi-walled carbon nanotubes, graphene, glassy carbon, boron-doped diamond, pyrolyzed photoresist films, and others known in the art.

Additionally, all of the above carbon allotropes may be dispersed in powder form in a suitable binder, or formed in-situ on the surface of the WE. Such binders include organic or inorganic polymers, and adhesive materials. In some embodiments, the substrate is graphite powder and the binder is epoxy resin. In other embodiments, the substrate is a graphite rod. In other embodiments, the substrate is an isotropic graphite solid. In other embodiments, the substrate is a carbon fiber composite. In other embodiments, the substrate is a graphite-filled polymer exemplified by, but not limited to, polyphenylene sulfide, polysulfone, or polyvinylidene fluoride. In other embodiments, the substrate comprises a surface coating of an ink formulated with one or more carbon allotropes. In other embodiments, the substrate comprises a surface coating of an ink formulated with one or more metals exemplified by silver, gold, and platinum. In other embodiments, the substrate is an ionomer. In other embodiments, the substrate is an ionomer containing a dispersion of carbon allotrope particles, carbon nanotubes, carbon nanowires, graphene, metal, or other compatible agents for enhancing the physical and electronic properties of the matrix including, but not limited to, assisting transmission of electronic signals from the RAM.

The WEs (and AIEs) of the present invention may be configured so as to be removable from the probe, allowing them to be easily interchanged or replaced according to the required design and functionality. The WEs of the invention can be configured and programmed to replace a traditional glass probe in a traditional pH meter and/or to generate a signal that is transmitted by electrical wiring, or via electromagnetic means not requiring wires, to a readout device (see PCT Application No. US2013/023029, incorporated herein by reference).

The pH or other analyte probe of the invention may further include a reference electrode (RE). A number of conventional reference electrodes suitable for use in a probe of the present invention are known in the art. See, for example, Bard and Faulkner, "Electrochemical Methods: Fundamentals and Applications" (Wiley 2001), incorporated herein by reference.

In some embodiments of the invention, the conventional reference electrode is a chloridized silver wire surrounded by an electrolytic solution. In other embodiments, the conventional RE is only a chloridized silver wire. In other embodiments, the conventional RE is an iodide/tri-iodide system as described in U.S. Pat. No. 4,495,050, incorporated herein by reference. In other embodiments, the conventional RE is a standard calomel electrode.

The present invention also provides a variety of embodiments in which a solid-state working electrode (WE) featuring a redox-active analyte-sensitive material is operated in conjunction with a conventional RE or PRE in the same pH metering system. This hybrid approach combines the robustness inherent in solid-state devices and the accepted reference standard upon which much of electrochemistry science is based. In some embodiments of the invention, a nonporous material is used as a junction between the analyte and the internal reference solution of the RE or PRE. The nonporous material is selected to provide passage to ions but is resistant to convective flow, thereby minimizing the likelihood of composition change in the reference solution due to mixing with the analyte, or in certain cases chemical interaction with substances in the analyte resulting in precipitation or clogging of the junction. The consequence of such mixing or interaction is a change in the chemical environment of the reference redox couple, and thus a shift in the reference potential. In a specific embodiment of the invention, the reference junction material comprises an RTIL, a polymer at least partially miscible with RTIL, and optionally a carbon allotrope compounded to provide good mechanical stability in addition to the electrochemical and barrier properties described above.

A "counter-electrode" or "CE," also sometimes referred to as an "auxiliary electrode," is an electrode that is required, in some analyte sensors, to pass current through the electrochemical cell to complete the electrical circuit. The CE serves as a source or sink of electrons and allows current to flow through the WE to effect the redox reaction. To avoid unwanted electrochemical redox processes, CEs are typically made using chemically inert conductors, commonly stainless steel or other specialty alloys, carbon and its composites, certain conductive polymers, or noble metals. All embodiments of the present invention may include a CE.

In various embodiments of the invention, the sensor also includes a temperature sensor such as a resistance temperature detector (RTD), thermistor, or thermocouple. The pH of a sample is a function of temperature; therefore, it is often important to measure and monitor the temperature of an analyte rapidly and accurately. In some embodiments, the sensor cluster comprises a thermistor that is embedded into the reference junction. In another embodiment, the sensor cluster comprises a thermistor that is located close to the analyte, the working electrode, and the reference electrode, preferably in contact with materials of high thermal conductivity, such that the temperature of the analyte sample is quickly and accurately measured. In other embodiments, a thermistor is embedded directly beneath a Type 316 stainless steel counter electrode (see FIGS. 5 and 6).

Figure 1:
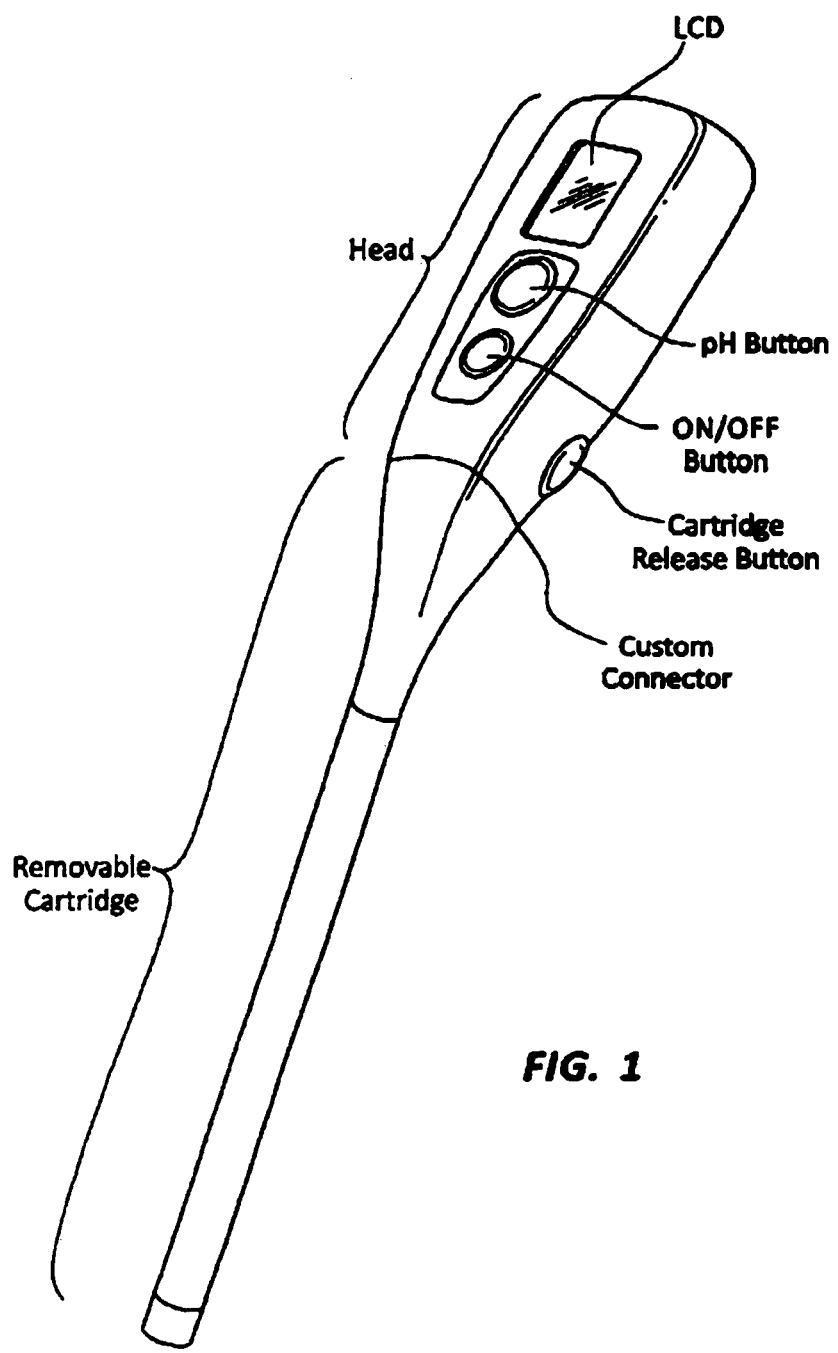
FIG. 1 shows an illustrative hand-held pH meter (sometimes referred to herein as a "scanner") of the invention composed of a detachable head having an LCD display, operator control buttons, and a cartridge release button connected via a custom connector (see FIG. 2) to a removable cartridge comprising the electrodes in accordance with a representative embodiment of the invention.

In other aspects, the present invention provides hand-held pH meters ("scanners") containing one or more electrodes as described herein. The hand-held pH scanners of the invention are calibration free solid state pH meters. The instrument's architecture maximizes the flexibility with regard to form factor, working environments, and applications. In some embodiments, the system has a head unit that contains buttons for user input, a display screen, and a custom connector to facilitate attachment and replacement of removable sensor cartridges (see FIGS. 1 and 2). In some embodiments, the removable cartridge containing the sensor cluster has a 12 mm diameter tube to house the sensor cluster and related electronic circuitry. Typical glass pH electrodes have been standardized with a 12 mm diameter. Many laboratory and process fixtures are designed to accommodate the 12 mm diameter form factor. This embodiment of the invention is designed to be suitable for use in these use environments (see FIG. 3).

Figure 7:
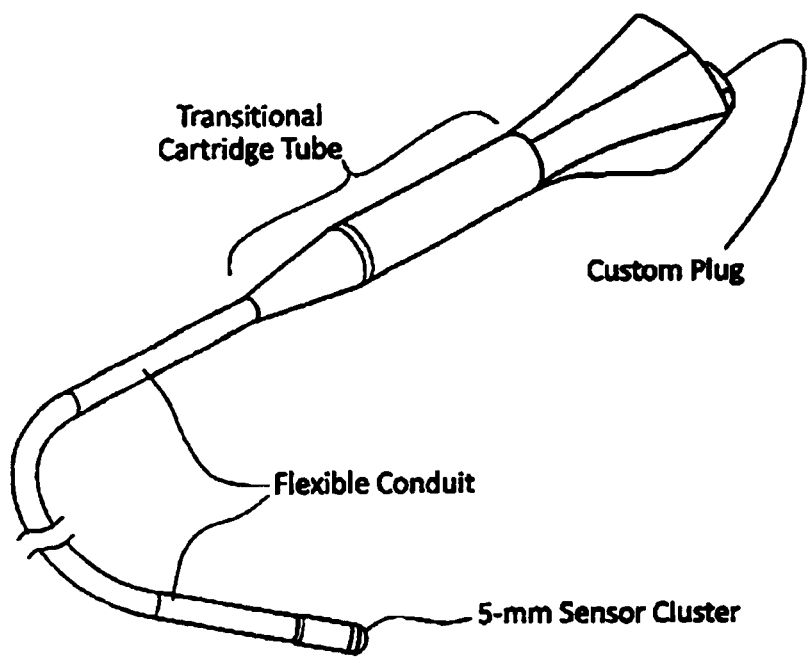
FIG. 7 shows an embodiment of a flexible and user configurable sensor cartridge containing a 5-mm sensor cluster (see FIG. 9), a flexible conduit, a transitional cartridge tube, and a custom plug in accordance with a representative embodiment of the present invention.

Another illustration of the range of form factors provided by the invention is a sensor cartridge embodiment that is flexible, and so is user-configurable, in a "gooseneck" fashion. As sensor cartridges of the present invention do not require the use of glass, there is no associated restriction for rigid shapes of limited length. Instead, sensor cartridges and probes can be connected to the head unit with various cabling and connectors. See FIG. 7. Voltammetric sensors of the invention can be manufactured with lengths much longer than possible with glass electrodes, which rarely exceed a fraction of a meter. With suitable signal boosting circuitry, rigid or flexible sensors of the invention can be on the order of ten meters. Typical lengths include 0.25, 0.5, 1, 2, 5, and 10 meters, for example and without limitation.

Figure 8:
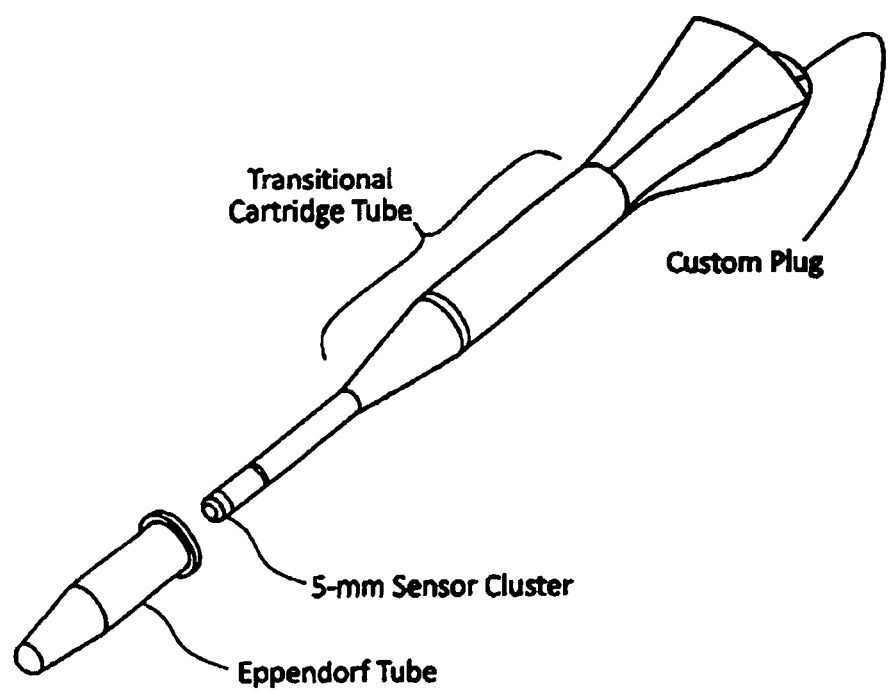
FIG. 8 shows a 5-mm diameter sensor cartridge that fits into a container such as an Eppendorf tube. The sensor cartridge contains a sensor cluster (see FIG. 9), a custom plug, and a transitional cartridge tube in accordance with a representative embodiment of the present invention.

In another embodiment, the removable cartridge of the invention is provided in the embodiment of a smaller 5 mm sensor cluster suitable for measuring the pH of samples in small containers, for example, Eppendorf tubes or the wells of a multi-well plate. This smaller form factor is shown in FIG. 8.

Figures 3A, 3B:
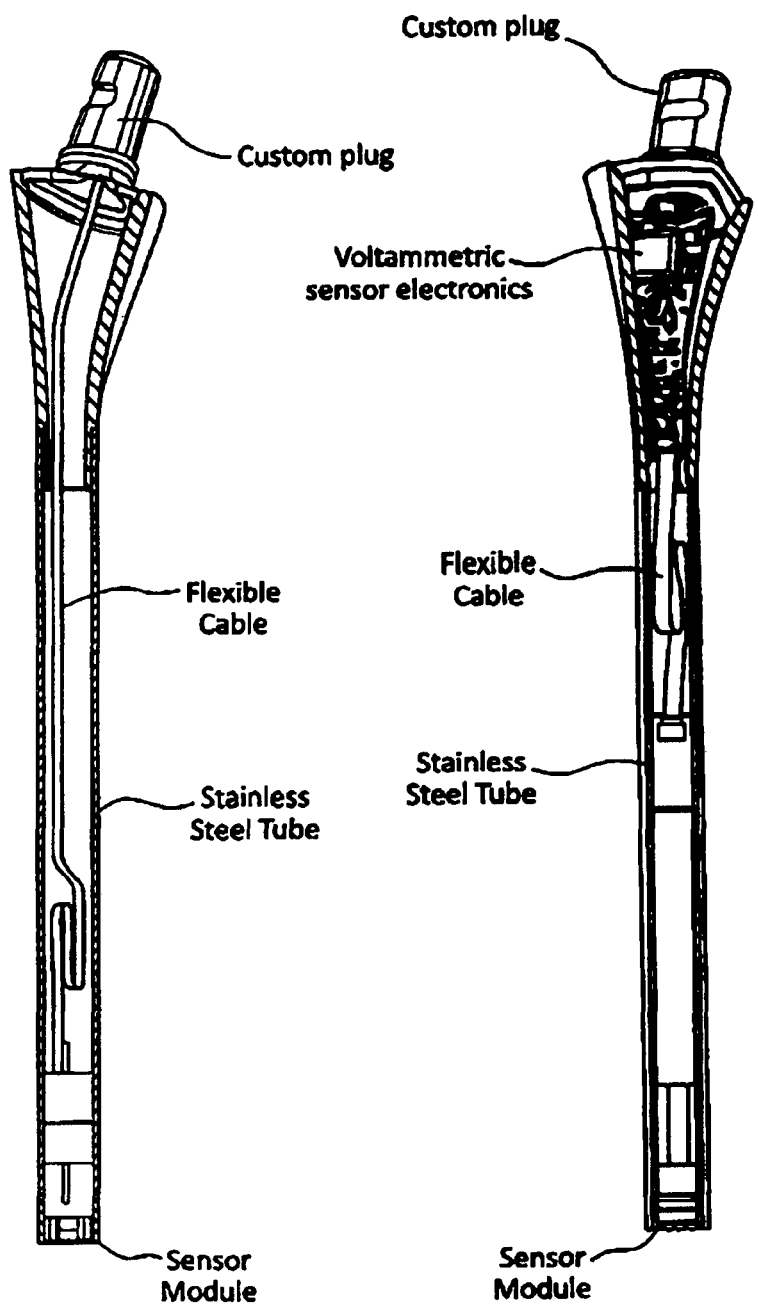
FIG. 3A shows a sensor module connected to a flex cable that connects directly to the custom plug.
FIG. 3B shows a sensor module that is connected to the voltammetric sensor electronics. Both embodiments have a protective stainless steel tube with a 12-mm diameter.

In other aspects, the present invention provides multiple packaging options for the electronic circuits and components to meet various requirements. In some embodiments, the sensor cartridge comprises the housing, the sensor cluster, a connector that mates with the head unit, and wiring between the sensor cluster and the connector, as depicted in FIG. 3A. In an alternate embodiment, a small circuit board carrying preamplifier and/or analog-to-digital converter and optionally power regulation components is connected directly to the sensor cluster, as depicted in FIG. 3B. In some embodiments, the cartridge housing is a rigid conduit. In another embodiment, the cartridge is a flexible conduit (see FIG. 7) made from a flexible material, which can be, but is not limited to, PVC tubing (e.g., Tygon B-44-3), EPDM rubber, silicone rubber, fluoroelastomers, fluoropolymers, polyurethanes, blends, and copolymers thereof. Selection of material is dependent on the targeted application. In some embodiments, the flexible conduit is user configurable by means of a gooseneck tube made, for example, of reinforced or braided stainless steel (e.g. Hagitec WCD series, MCD series, and CD series). In other embodiments, the cartridge housing comprises shielded and optionally armored cabling designed to minimize electromagnetic interference, and to resist environmental damage. More generally, locating preamplifiers and/or analog-to-digital converters close to the sensor cluster increases signal strength and thus increases the transmission distance that can be employed. The maximum length of a flexible probe of the invention is limited largely by signal degradation and electromagnetic noise or interference. In practice, flexible pH probes of the present invention 1 m in length or longer (e.g. 10 meters or longer) enable precise measurement indistinguishable from their rigid, shorter counterparts.

In other aspects of the invention, the sensor cluster and all electronics are located together in a compact, self-powered measurement device wherein the operation of the system and retrieval of measurement results are performed remotely by wireless communication. Various embodiments are suited for deployment in conjunction with telemetry or remote sensing technology. The telemetry/remote sensing module, equipped with antennas and integrated electronics, can perform any of several functions, including wireless communication and geographical positioning. It also establishes a link for remote control of the operation of the voltammetry sensor electronics. One specific embodiment provides a system mounted on a floating platform wherein the voltammetric sensor is located on the bottom of the platform in a rigid or flexible probe submerged in the analyte, typically water, to a depth specified by the user. This design is particularly suited for measuring pH in bodies of water for environmental monitoring or for water analytics associated with water supply, waste treatment, oceanographic research, and waterway management. In other embodiments, the sensor cartridge or functionally equivalent structures and voltammetry sensor electronics are submerged to various depths below the water surface, while the telemetry/remote sensing components are exposed on the water surface to enable efficient signal up/downlink. In yet other embodiments, multiple sensor cartridges are arranged in a matrix covering a defined space to enable mapping of pH gradients and their variations over time.

Other terrestrial applications include monitoring of soil samples or the surveillance of irrigation run-offs. In other embodiments, an array of sensor cartridges is deployed to characterize soil pH at multiple locations, analogous to the method provided for water analytics described above. Such applications are exemplary of the myriad uses enabled by the advantages of this invention, especially the robustness and ability to render analyte information precisely in a manner unaffected by drift, maintenance, and location concerns. FIGS. 4A and 4B schematically illustrate two embodiments of these systems deploying rigid and flexible sensors of this invention, respectively. In other embodiments, the voltammetric sensors of the invention are built into protective housings such as water-proof enclosures for the voltammetry sensor electronics and battery pack for oceanographic applications, or mechanical reinforcement such as corrosion resistant housings for subterranean placement.

In various embodiments, the hand-held pH meter features one or more of the following attributes: (i) the sensor cartridge is detachable and replaceable; (ii) the sensor cluster in the sensor cartridge is detachable and replaceable; (iii) the sensor cluster and associated electronic circuit components are provided in removable cartridges of different form factors (e.g. 5 mm or 12 mm diameter), each designed with connectors compatible with the head unit described herein. In other embodiments, one or more of the components identified as replaceable above is instead a fixed component.

The use of various sensor cartridges described herein is not limited to hand-held pH scanners. Instead, the sensor cartridges of the invention can be utilized in instruments and systems equipped with suitable connectors to accept them. These include form factors of bench-top instruments, industrial transmitters and controllers, and subsystems of other instruments and processors with suitable interface hardware and algorithms.

The present invention also provides methods and components that provide improved signal processing. Square wave voltammetry is a well-established electroanalytical technique that allows correlation of the current in an electrochemical cell with the concentration of the solution species of interest. Its principles, operation, and applications have been described in detail. See, for example, "Square Wave Voltammetry," J, G and R. A. Osteryoung, Analytical Chemistry 57, (1) 1985, 101A-110A; "Theory of Square Wave Voltammetry" and "Analytical Applications of Square Wave Voltammetry," L. Ramaley and M. S. Krause, Analytical Chemistry 41, 11 (1969) 1362-1365. Various commercial instruments currently available implement square wave voltammetry in various electronic designs that typically share the capability of defining key operating parameters as well as common benefits of producing rapid, sharp peak measurements and effective rejection of errant signals from irreversible redox processes.

Figure 10:
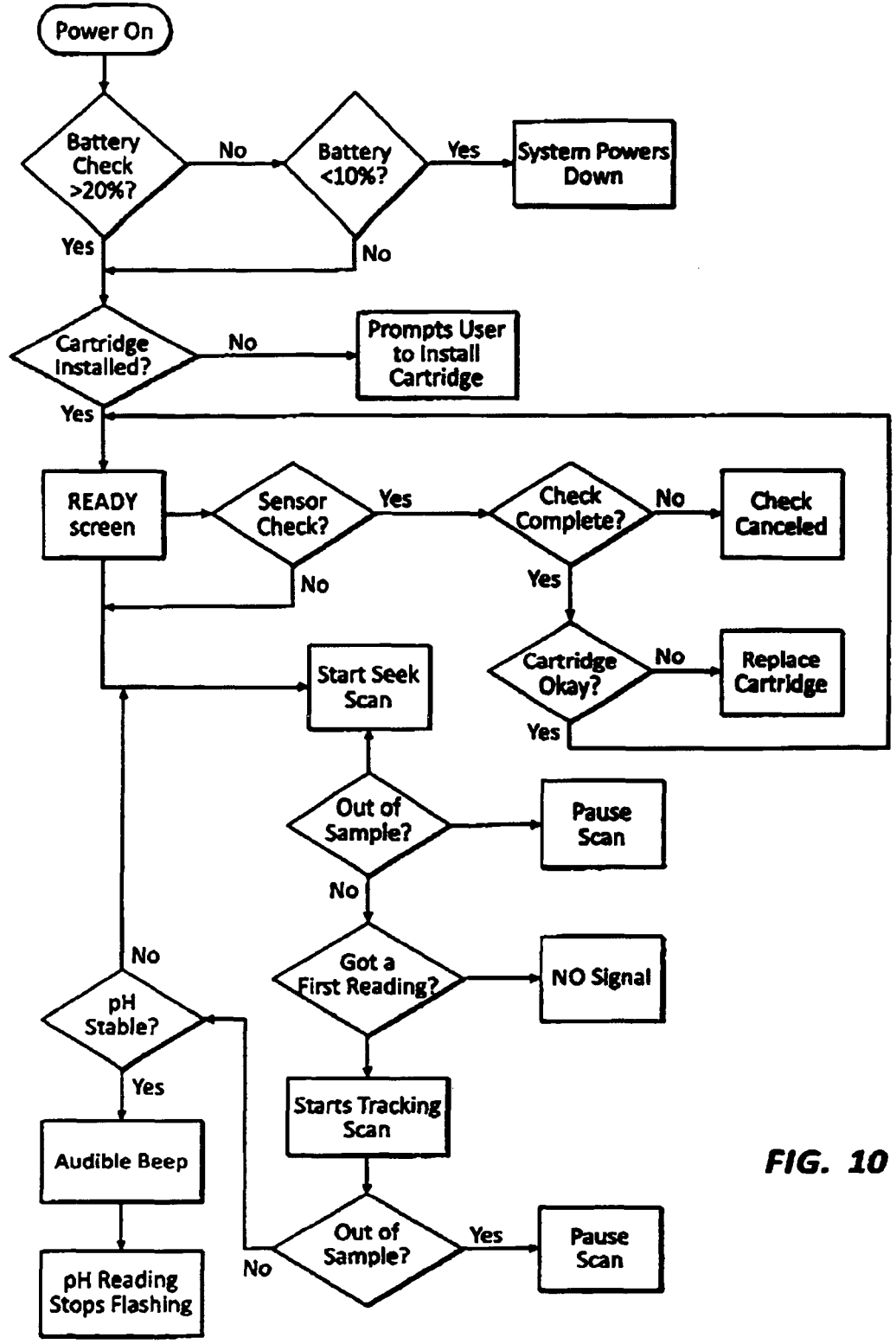
FIG. 10 shows a logical flow diagram for a user interface of a hand-held pH meter in accordance with a representative embodiment of the invention.

The implementation of signal processing electronics and methods of the present invention delivers functionalities comparable to other commercial systems and also provide ease of use and a simple user interface (UI) in a hand-held instrument. Various aspects of the UI provide control of the operation of the scanner, display key measurement results, display power supply status, transmit data, or program the device. FIG. 10 is a logic flow diagram showing the command structure, system response to various events, and display of measurement information and system status. The firmware of the system provides the following major functions: (1) Power on/off control; (2) System check, which verifies the battery status, and the presence of a sensor cartridge connected to the head unit; (3) Sensor check, which determines the conformance of the sensor cartridge to a pre-selected reference point within an internal correlation database, and corrects for any deviation therefrom (in a specific embodiment, the working electrode potential measured in a pH 7 buffer solution is compared to the value derived from a standardized group of cartridges with the same type of WE and RE and stored in the firmware in the head unit); (4) pH measurement, where a voltage scan sequence in accordance with preset square wave voltammetry conditions is initiated, and the response from the sensor cartridge collected and processed; (5) Error trapping, where the system detects (i) a loss of contact between the sensor and the analyte, and reports the condition with an "Out of Sample" message; (ii) a useable signal is not generated by the sensor cartridge; or (iii) other operational irregularities; (6) User-selectable display of pH, temperature, peak potential, and signal strength; and (7) System indicators, including battery charge level, scan progress indicators, and other visual indicators of system status.

For analyte concentration, i.e., pH measurement, the invention provides, in some embodiments, a broad voltage range (scan window) that is first used to determine the approximate location of the current peak, encompassing a large portion of the pH scale (for example pH 2-12); this is referred to as the "seek scan." Thereafter a sequence of scans is performed using a narrower scan window dynamically defined to bracket the initial value on the potential scale. These measurements are referred to as "track scans" and are performed at higher voltage resolution than that of the seek scan to achieve high accuracy. A number of successive potential measurements are compared on a rolling average basis until consecutive averages differ less than a threshold, whereupon the measurement is considered stable and accordingly displayed and an audible signal generated.

The vast majority of pH meters on the market today utilize potentiometric pH probes that require a complex user interface to deal with the highly technical aspects of initial set-up, maintenance, and calibration of the probe. These pH meters require the user to establish key aspects of calibration including the response of the probe to pH (slope) and variability in the reference electrode (the y-intercept). To calibrate a traditional pH probe, the user must expose the probe to a series of buffer standards of varying pH and operate the user interface of the device so that the calibration information is properly input into the device before measuring the pH of a sample of interest. Due to the complex and technical nature of the calibration and other set-up procedures, pH meters are typically used primarily in a laboratory environment with highly skilled technicians. Even still, there is potential for mis-calibration and other errors in setting up a pH meter, resulting in errant pH readings that may be unknown to the user. Many field applications in agriculture, such as measuring the pH of soil or fruit in the field (useful for determining harvest timing), or environmental monitoring applications such as measuring the pH in rivers, ocean reefs and industrial effluents go unmeasured or under measured due to the complexities of operating currently available pH measuring equipment and the fact that the users in these environments may not be classically trained chemists or operators.

The calibration free and mechanically robust nature of the voltammetric sensor described herein enables coupling of the sensor cluster to the first full featured user interface capable of being operated through the use of only two buttons and enables for the first time a user with virtually no technical training whatsoever to measure pH with accuracy and precision equal to or better than the best potentiometric (glass) pH meters on the market today. The user interface provided by the invention is extremely simple to use and enables the user to measure the pH of a sample of interest with a single button push, a unique feature impossible to replicate with conventional pH meters. In addition, the invention provides error trapping features that can be built into the pH meter to notify the user if the sensor is not in contact with the sample or if the signal from the sensor is too weak to be relied upon for accurate pH measurement. For the first time, highly accurate pH measurement is made possible even for the untrained user through a dramatically simplified user interface comprising only two buttons coupled with sophisticated programming that runs automatically upon simple button push combinations described in detail below. In some embodiments, the pH meter or scanner has only two buttons: a "power on/off" button and a "pH" button. The user interface (UI) provided by the invention operates under the control of short and long presses of the pH and Power buttons. With the combination of the aforementioned buttons and an LCD screen, the user is able to perform every function available on the pH meter, which may be in the form of a handheld scanner.

In some embodiments, the scanner is powered on by pressing the power button, which initializes the system firmware followed by an audible signal and the display powers on. At this point, the firmware detects the presence of the sensor cartridge, including the thermistor and the charge level of the battery. Upon completion of the internal test, the display shows "Ready" and the scanner is ready for use. The meter can be powered down by long pressing (>7 seconds) the power button from the Ready screen.

A user performs a pH (or other analyte) measurement by pressing and holding the power button of the pH meter to power on the unit. The user then rinses the sensor of the pH meter, such as by running deionized water or another cleaning agent over the end of the pH meter probe. The user then inserts the sensor end of the pH meter into a sample. With the sensor end of the meter positioned in the sample, the user presses the pH button of the pH meter to initiate a scan of the sample. If the user desires to perform a pH measurement on a different sample, the user repeats the step of rinsing the sensor prior to inserting the sensor end of the meter into the new sample and initiating a new scan. A user may terminate a scan in progress by pressing the pH button at any time during the scan. The programming described below is designed so that the user simply pushes the "pH" button, which triggers the running of a series of algorithms resulting in a high precision pH measurement from a single button push. From the Ready screen, pressing the pH button initiates a pH measurement wherein the sensor undergoes a voltage scan sequence. Throughout the pH measurement process, the LCD screen displays the pH reading of the sample, the temperature of the sample, and the battery level. As more briefly described above, the scanner can be programmed to perform two types of scans: a Seek Scan, and a Track Scan. Generally, in a voltammetric sensor of the invention, the change in peak current location over the voltage range resulting from a change in pH will be about 60 mV per pH unit. The Seek Scan is, in some embodiments, a low resolution, e.g. 4 mV (~0.066 pH unit), wide range, e.g. >600 to 1200 mV (e.g. a measurable range of from approximately 7 to 14 pH units), scan enabling the meter to detect the pH of a sample quickly (i.e. circa 15 seconds) across the entire pH range of 0 to 14 or, optionally, some portion of that range (typically 7 or more pH units). For example if the sensor is placed in a process stream where the pH range is relatively well known (e.g. milk at pH 6.6) the voltammetry sensor electronics could be tuned to scan a center point based on an expected pH value (6.6 in the case of milk, but the center point can be any pH value) plus and minus a range (i.e. 1 pH unit, or a range of 5.6 to 6.6, in the case of a pH 6.6 center point, but the range can be any range between 0 and 14) thereby enabling more rapid updates of the display. This approach enables more scans per unit time by limiting the pH range of each scan. Once the peak position is established by the Seek Scan, a series of Track Scans is initiated. Track Scans are high resolution, e.g. 2 mV (~0.033 pH unit), scans within a narrow range, e.g., 200 to 600 mV (a measurable range of 3 pH units), with the center of the range at the voltage corresponding to the peak position obtained from the Seek Scan. In various embodiments, the narrow range is +/−300 mV from the voltage corresponding to the peak position obtained from the Seek Scan. See FIGS. 12A and 12B.

In some embodiments, when the user pushes the pH button, the scanner performs an initial Seek Scan. While the Seek Scan is being performed, four dashed lines are shown on the display in flashing mode to indicate that the pH reading is currently unknown. Once the Seek Scan has determined the approximate pH value, that value is shown on the display in flashing mode indicating to the user that a stabilized reading has not yet been reached. The scanner then automatically performs a series of Track Scans and the values obtained from each Track Scan are incorporated into a rolling average of, e.g., three successive readings, where the variation is less than a specific value predetermined but adjustable in the algorithm. For example, a variation of less than 6 mV corresponds to a 0.1 pH unit precision, and a 2 mV variation corresponds to a 0.03 pH unit precision.

At this point, the measurement is considered stable, and the pH value is displaced as a steady value. At the same time, an audible sound is emitted to let the user know that the scanner has stabilized on the pH value. If subsequent measurements from a Track Scan cause the standard deviation to fall outside a preset limit, the scanner reverts back to the Seek Scan mode, and the process is repeated with following Track Scans until a stabilized reading has once again been achieved.

Additional measurement data such as peak potential in millivolts (mV) and peak current in microamps (µA), can be viewed with a short press (i.e., 1 second) of the power button once the Track Scan has stabilized. Another short press of the power button toggles back the display to pH and temperature. Even after a stabilized reading has been reached, the scanner continues to perform Track Scans and update and display the rolling average. If the user wishes to stop scanning the sample, this is accomplished with a short press (i.e. one second) of the pH button. The display then shows "Last Reading" along with the values for pH, temperature, peak potential, and peak intensity. A second short press of the pH button returns the display to the "Ready" screen.

The WE of a sensor cluster has a finite lifetime based on the nature and frequency of samples being tested. Therefore, it is useful to enable the user to assess the status of the sensor on a periodic basis. This is accomplished by placing the sensor in a known buffer standard, such as pH 7 buffer, and executing a long press (i.e. 3 seconds) of the pH button. A status bar is shown on the display and the scanner performs 5 sequential high resolution scans (i.e. Track Scans) and compares the average of the five readings to a pre-selected reference point within an internal correlation database and corrects for any deviation therefrom. A unique feature of a properly functioning voltammetric sensor is that the response of the ASMs to pH (i.e. the slope) never changes; therefore, this embedded functionality within the Sensor Check feature corrects for any changes that may have occurred in the reference electrode (RE) by automatically resetting the y-intercept for the user. The Sensor Check also measures the signal strength (peak intensity in $\mu A$) of the scans to evaluate the status of the sensor, where a low signal indicates either the analyte is difficult to measure, or that the sensor is approaching the end of its service life. Once the Sensor Check is completed, the screen displays the signal strength that has been determined from the scans. In some instances, a recommended threshold for signal strength is 15 $\mu A$. Accordingly, if a value of 15 $\mu A$ or less is shown on the pH meter display, the user will replace the sensor cartridge. The user will then perform the sensor check, as described, using the new cartridge. Following successful completion of the sensor check, the user presses the pH button to return to the home screen of the pH meter. If the user wishes to abort the Sensor Check, a short press of the pH button cancels the process and returns the display to the "Ready" screen.

Unlike conventional potentiometric pH probes, the scanner provided by the invention is able to detect and display messages that help the user to reduce measurement error and obtain more reliable results. For example if the sensor is not in contact with a sample, the display will show "Out of Sample", thereby letting the user know to adjust the position of the sensor or sample. This is accomplished by detecting the DC current of the sensor. See FIG. 13. The "Out of Sample" feature can be triggered during pH measurement or Sensor Check function.

Additionally, the scanner is able to detect and display a message if the sensor is not returning a sufficiently strong signal for a reliable reading. This is accomplished by comparing the peak signal strength to a minimum, e.g. 2 $\mu A$, threshold. See FIG. 14. The "No Signal" feature can be triggered during pH measurement or Sensor Check. When triggered, the pH measurement or Sensor Check is terminated and the screen displays "No Signal," thereby letting the user know that the sensor is not able to measure the pH of that sample reliably.

Additionally, the scanner can be equipped with a Shutdown Timer function. The purpose of the Shutdown Timer is to notify the user if the scanner has been sitting idle for an extended period of time (i.e. greater than 5 minutes). The Shutdown Timer can be triggered from the "Ready" Screen, the "Last Reading", "No Signal", "Out of Sample" screens, and at the end of the Sensor Check and is intended to preserve battery life. When the Shutdown Timer feature is triggered, the display shows "Shutting Down". The user can cancel the shutdown with a short press of the power button that returns the scanner to the "Ready" screen. If the user does nothing, the scanner automatically powers down. A unique feature of the Shutdown Timer is that if the scanner was displaying a stabilized measurement at the time the Shutdown Timer was triggered, the last reading will be displayed when the scanner is powered back up. This unique feature ensures that the user does not experience any unintentional loss of data as a result of an automatic shutdown.

Figure 11:
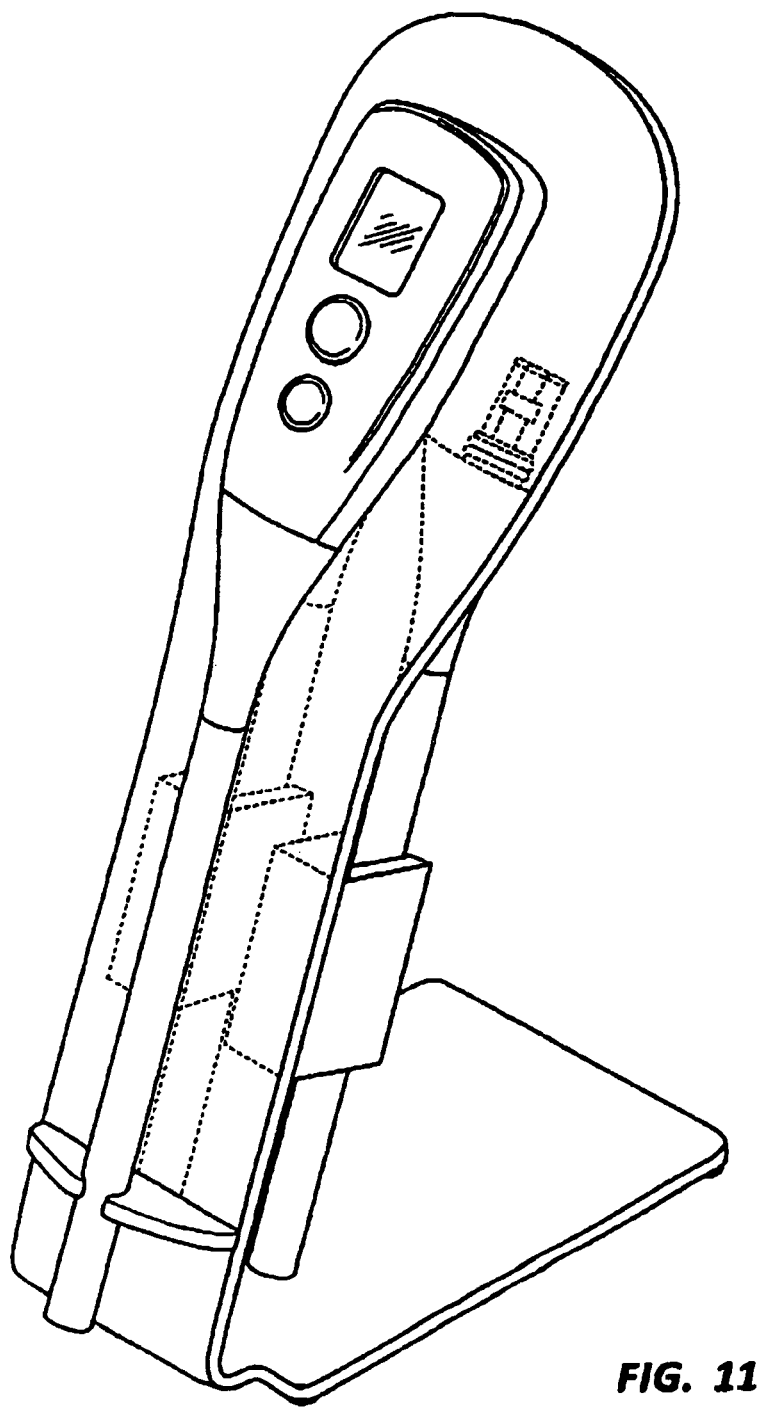
FIG. 11 shows a stand for a hand-held pH meter of the invention in accordance with a representative embodiment of the invention. In the embodiment shown, the stand has a bottom and upright plate, and the upright plate includes snap-fit holders on its front face for the fully assembled pH scanner as well as two optional sets of snap-fit holders on its back face for replacement sensor cartridges.

The present invention also provides a variety of stands suitable for holding the hand-held pH meters of the invention. FIG. 11 shows an illustrative embodiment of a stand for a hand-held pH meter of the invention. In the embodiment shown, the stand has a bottom and upright plate, and the upright plate includes snap-fit holders on its front face for the fully assembled pH meter as well as, optionally, two sets of snap-fit holders on its back face for replacement cartridges. Other embodiments of the stand include those in which there are more, fewer, or no snap-fit holders on the back face of the upright plate.

Those of skilled in the art will appreciate that there are many alternative ways of implementing and realizing the many benefits and advantages afforded by the various aspects and embodiments present invention. Accordingly, the present embodiments are to be considered as illustrative and not restrictive, and the invention is not to be limited to the details given herein, but may be modified within the scope and equivalents of the appended claims. All publications and patents cited herein are incorporated by reference in their entirety. The following examples are provided for illustrative purposes only and do not limit the scope of the invention.

Example 1

Sensor Cartridge

A sensor cartridge was constructed comprising the following components: a 12 mm OD×150 mm cartridge tube of Type 304 stainless steel (MicroGroup, Medway, Mass.); a mechanical and electrical connector designed to mate with the head unit (Amphenol, Wallingford, Conn.); a voltammetric sensor comprising a working electrode comprising an ASM functional surface based on AQ-PVA chemistry immobilized on a carbon fiber substrate (ACP Composite, Livermore, Calif.), a reference electrode comprising an Ag/AgCl/KCl system, a counter electrode fabricated from Type 316 stainless steel, and a thermistor (QTI, Boise, Id.) arranged as a cluster and mounted at the distal end of the cartridge housing. A ribbon cable connected the voltammetric sensor to the mechanical electrical connector that interfaces with the head unit. The arrangement of these components is shown in FIG. 3A. A sensor cartridge of this design was connected to an Autolab potentiostat and tested in pH 7 buffer solution (BDH) at 25° C. The working electrode peak potential and signal strength were monitored as functions of time. Results are shown in FIGS. 15 and 16. Over the course of 87 hours the potential remained within about 2 mV, corresponding to about 0.03 pH units. This stability is superior to that of conventional glass electrodes.

The working electrode potential of this sensor cartridge exhibited the linear relationship with analyte pH and temperature shown in FIG. 17. This correlation is the basis of conversion of measured potential to pH.

Example 2

Sensor Cartridge with Integrated Electronics

A sensor cartridge was constructed comprising the following components: a 12 mm OD cartridge tube of Type 304 stainless steel (MicroGroup); a mechanical and electrical connector (Amphenol) designed to mate with the head unit; a voltammetric sensor comprising a working electrode, a reference electrode, a counter electrode, and a temperature sensor arranged as a cluster and mounted at the distal end of the cartridge tube. A printed circuit board was provided on which are mounted preamplifier, analog-to-digital converter, power regulators, support logic, and other passive components. The circuit board was connected to the voltammetric sensor. A ribbon cable connected the printed circuit board to the mechanical electrical connector that interfaces with the head unit. The arrangement of these components is shown in FIG. 2B. This sensor cartridge of this design was tested under conditions similar to those of Example 1. The results summarized in FIG. 18 shows that the mV-pH correlation is not significantly affected by the location of the electronic circuitry relative to the sensor cluster.

Example 3

Voltammetric Sensor with a Modified Ag/AgCl Reference Electrode

Figure 5:
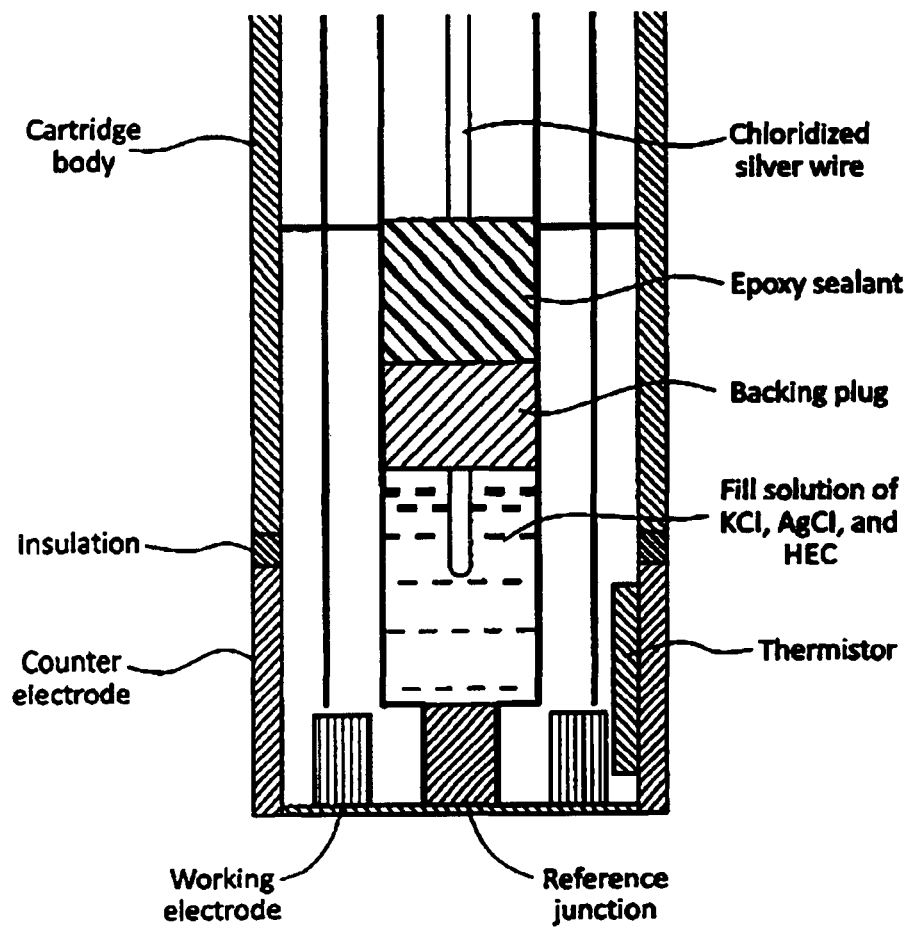
FIG. 5 shows a 12-mm sensor cluster comprising a Type 316 stainless steel counter electrode (CE), a carbon fiber working electrode (WE), and a modified reference electrode all located on the same plane in accordance with a representative embodiment of the present invention. This coplanar arrangement allows for small volume measurements due to an analyte sample surface being in contact with all three electrodes. The sensor cluster also contains a thermistor located directly beneath the CE for improved thermal conductivity.

A sensor cluster was constructed with a working electrode in the form of an annular ring fabricated with isotropic carbon (TTK4, Toyo Tanso). This substrate was functionalized with an immobilized AQ-PVA chemistry. The sensor cluster also included a reference electrode constructed with a tubular capsule containing 3M KCl solution, a saturated concentration of AgCl (containing excess AgCl solid), and hydroxyethyl cellulose (Cat. No. 434981, Sigma Aldrich) added as a thickening agent. One end of the tubular capsule was terminated with a composite polymer plug fabricated from a homogeneous mixture of 2 g of polyvinylidene fluoride (Kynar 721, Arkema), 1.6 g of room temperature ionic liquid (IL-0045, Iolitec), and 0.25 g of graphite powder (Cat. No. 496596, Sigma-Aldrich). A chloridized silver wire was immersed in this solution. The other end of the tubular capsule is terminated with an epoxy sealant. The sensor cluster also included a counter electrode was constructed with 12 mm O.D. type 316 stainless steel tubing. A thermistor (QTI) was mounted at the inner surface of the counter electrode. A ribbon cable connected these electrodes to the mechanical and electrical connector. These electrodes were mounted concentrically to form a sensor, such that their sectional surfaces are co-planar to one another, as shown in FIG. 5. This modified Ag/AgCl reference electrode was evaluated by measuring its potential against a Cole-Parmer standard calomel electrode (SCE) in different standard buffer solutions ranging from pH 2 to pH 12. The results shown in FIG. 19 indicate that the modified Ag/AgCl reference electrode returned a stable reference potential over a wide pH range.

Example 4

Voltammetric Sensor with an Analyte-Insensitive Electrode (AIE)

Figure 6:
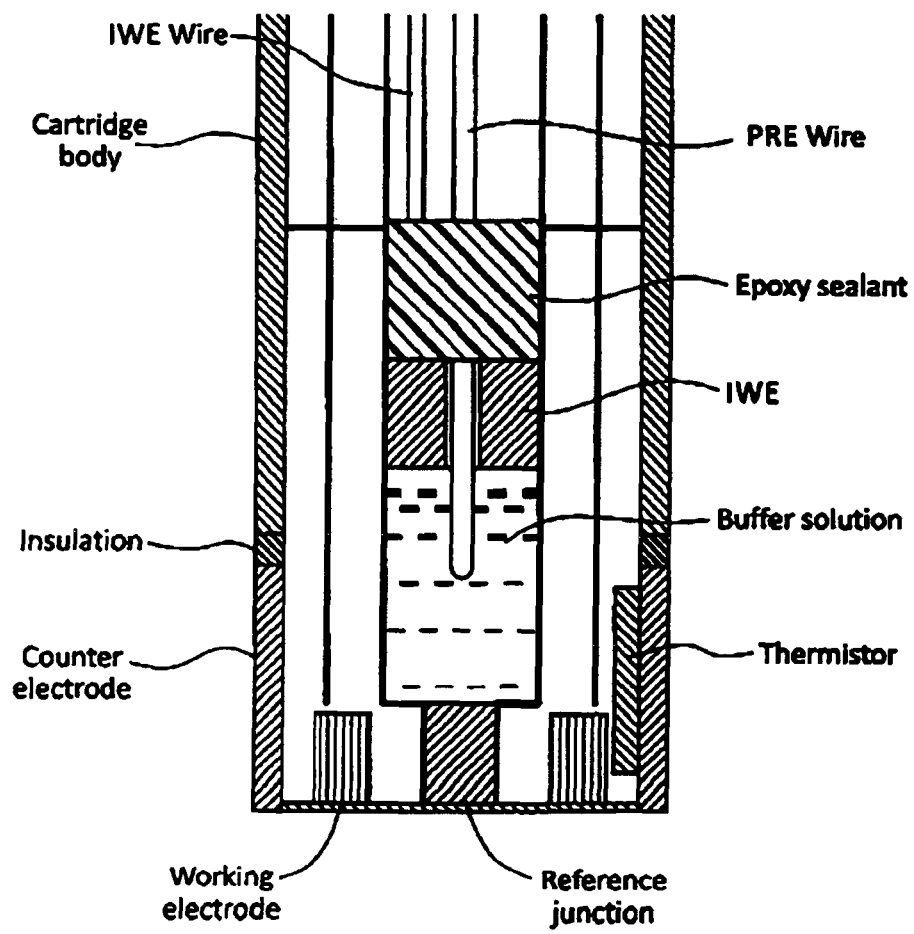
FIG. 6 shows some embodiments of a 12-mm sensor cluster comprising a Type 316 stainless steel CE, a carbon fiber WE, and an analyte-insensitive electrode (AIE), all located on the same plane. The AIE comprises a buffered solution, a pseudo reference electrode (PRE), and a carbon fiber internal working electrode (IWE). The sensor cluster also contains a thermistor located directly beneath the CE for improved thermal conductivity.

A sensor cluster was constructed with a working electrode in the form of an annular ring fabricated from carbon fiber composite, on which AQ-PVA was immobilized. The sensor cluster also included an AIE comprising an internal working electrode (IWE) of carbon fiber in the form of a solid cylinder with a polished end, on which AQ-PVA was immobilized. The IWE was mounted on one end of a tubular capsule containing a pH 7 reference solution (BDH), referred to in the current context as the internal reference solution. The internal reference solution also contained 5% by weight of hydroxyethyl cellulose as thickening agent. On the opposite end of the tubular capsule was an analyte barrier comprising a non-porous solid to allow passage of ions but not mixing between the analyte and the internal reference solution. The AIE included a pseudo reference electrode (PRE) consisting of a platinum wire immersed in the internal reference solution. The sensor cluster also included a counter electrode constructed with 12 mm O.D. type 316 stainless steel tubing. A thermistor was mounted at the inner surface of the counter electrode. These electrodes were mounted concentrically such that their sectional surfaces were co-planar to one another, as shown in FIG. 6. A voltammetric sensor constructed in this way was tested using pH 7 BDH buffer solution as analyte. The peak positions of the internal working electrode (PP IWE) and of the external working electrode (PP WE) were measured as a function of time, and the difference between these values (PP IWE-WE) was also calculated. Results are shown in FIG. 20. Notably, the differential signal was relatively unaffected despite differences in the individual potentials of the internal and external working electrodes due, for example, to unstable PRE potential. This characteristic of AIE-based voltammetric sensors provides an additional level of stability and fault tolerance.

Example 5

Flexible Sensor Cartridge

A flexible sensor cartridge comprising the following components was constructed. The cartridge had a housing consisting of a 1.2 m length of Tygon R-3400 tubing (7/16 inch ID, 1/16 inch wall thickness); a mechanical and electrical connector designed to mate with the head unit; and a voltammetric sensor comprising a working electrode, a reference electrode, a counter electrode, and an optional temperature sensor arranged as a cluster and mounted with a liquid-tight seal at the distal end of the cartridge housing. The flexible sensor cartridge is shown schematically in FIG. 7.

Example 6

A 5 mm Sensor Cartridge

Figure 9:
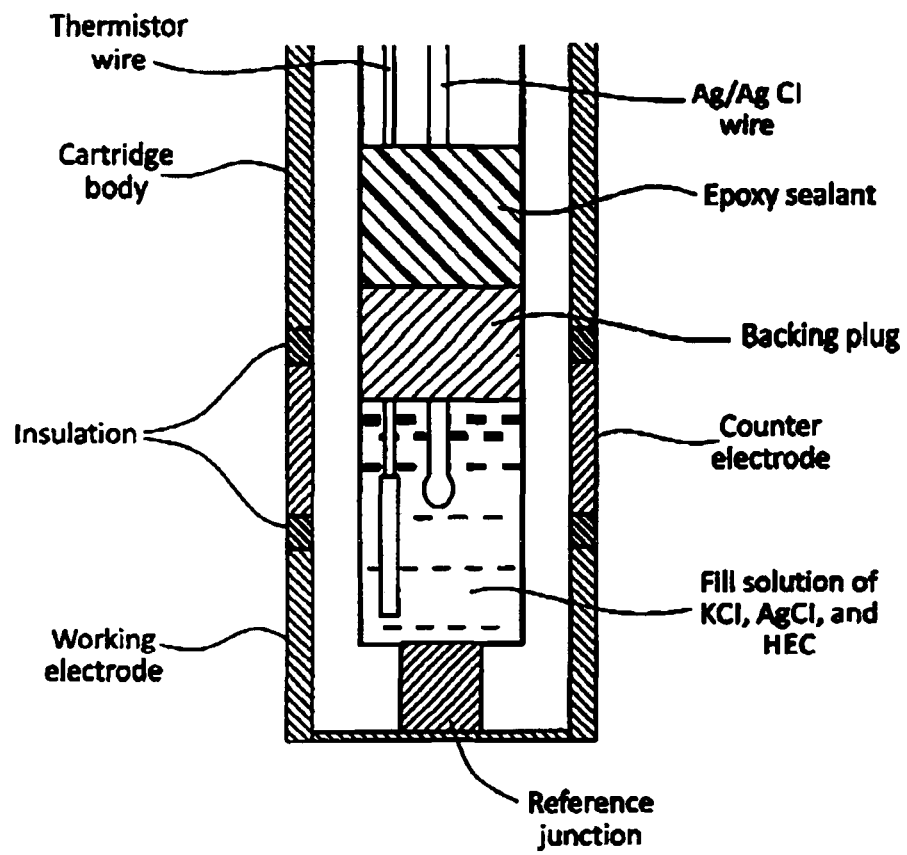
FIG. 9 shows a 5-mm sensor cluster comprising a CE, WE, RE, and a thermistor. In this embodiment, only the WE and RE are coplanar, while the CE is located behind the WE and separated from it by an insulating material in accordance with a representative embodiment of the present invention. This arrangement relies on analyte displacement to make contact with all three electrodes.

A sensor cartridge was constructed comprising the following components: a 12 mm OD×125 mm cartridge housing of Type 304 stainless steel (MicroGroup) that transitions down to a 5 mm OD; a mechanical and electrical connector designed to mate with the head unit (Amphenol); a voltammetric sensor comprising a working electrode (Carbon Fiber, ACP Composite), a reference electrode, a counter electrode (Type 316 stainless steel), and a thermistor (QTI) arranged as a cluster and mounted at the distal end of the cartridge housing. A ribbon cable connected the voltammetric sensor to the mechanical electrical connector that interfaces with the head unit. The arrangement of these components is shown in FIGS. 8 and 9.

The invention claimed is:

1. A hand-held analyte sensing device comprising a working electrode, a reference electrode, and a counter electrode, said working electrode, said reference electrode, and said counter electrode being concentrically arranged in a coplanar configuration;
- a first insulating material interposed between said working electrode and said reference electrode, said first insulating material separating said working electrode from said reference electrode;
- a second insulating material interposed between said working electrode and said counter electrode, said second insulating material separating said working electrode from said counter electrode;
- firmware and electronics operably coupled to the working electrode, the reference electrode, and the counter electrode for voltammetry and signal processing, and further comprising a display and controls for operating the device; and
- an internal working electrode positioned behind the reference electrode and separated from the reference electrode by a buffer solution.

2. The device of claim 1 with transmission capability.

3. The device of claim 1 with a temperature sensor.

4. The device of claim 1 that comprises a sensor cartridge connected mechanically and electrically to a head unit.

5. The device of claim 4, wherein said sensor cartridge comprises the working electrode, reference electrode, counter electrode, and a temperature sensor arranged in a cluster.

6. The device of claim 5, wherein said sensor cartridge comprises circuitry for signal processing.

7. The device of claim 5, wherein said sensor cartridge is contained in a flexible conduit.

8. The device of claim 4, wherein said head unit comprises electronic components for signal processing and information display through a user interface.

9. The device of claim 8, wherein said head unit has data transmission capability.

10. The device of claim 1, wherein said firmware can perform a seek scan at a low resolution over a wide voltage range and to determine an approximate location of a current peak, and once the approximate location is identified, can perform one or more track scans at a higher resolution and narrower voltage range than that of the seek scan to identify the current peak precisely.

11. The device of claim 1, that has two control buttons, one for powering the device on or off and the other to initiate an analyte sensing operation.

12. The device of claim 1, wherein said firmware can perform a sensor check and automatically correct for a change in the reference electrode.

13. The device of claim 1, wherein said firmware can perform a sensor check and inform a user if the device is functioning improperly.

14. The device of claim 1, wherein said working electrode comprises an immobilized analyte sensitive material.

15. The device of claim 1, wherein said reference electrode comprises a modified silver/silver chloride couple and a nonporous reference junction.

16. The device of claim 1, wherein said reference electrode is an analyte-insensitive electrode.

17. The device of claim 1, further comprising:
- a pseudo reference electrode having a distal end in communication with the buffer solution; and
- a third insulating material interposed between said internal working electrode and said pseudo reference electrode, said third insulating material separating said internal working electrode from said pseudo reference electrode.

* * * * *